(12) United States Patent
Bauta et al.

(10) Patent No.: US 6,664,401 B2
(45) Date of Patent: Dec. 16, 2003

(54) PROCESS FOR PREPARING ISOCOUMARINS

(75) Inventors: William E. Bauta, San Antonio, TX (US); William R. Cantrell, Jr., San Antonio, TX (US); Dennis P. Lovett, San Antonio, TX (US)

(73) Assignee: ILEX Products, Inc., San Antonio, TX (US)

( * ) Notice: Subject to any disclaimer, the term of this patent is extended or adjusted under 35 U.S.C. 154(b) by 0 days.

(21) Appl. No.: 10/188,556

(22) Filed: Jul. 2, 2002

(65) Prior Publication Data

US 2003/0105340 A1 Jun. 5, 2003

Related U.S. Application Data

(60) Provisional application No. 60/303,532, filed on Jul. 6, 2001, and provisional application No. 60/352,407, filed on Jan. 28, 2002.

(51) Int. Cl.[7] ............................................. C07D 311/02
(52) U.S. Cl. ...................................................... 549/283
(58) Field of Search ........................................ 549/283

(56) References Cited

U.S. PATENT DOCUMENTS 6,020,363 A     2/2000   Hirano et al. ................ 514/456

FOREIGN PATENT DOCUMENTS

| FR | 2579099 | 6/1988 | ......... C07D/311/76 |
| JP | 08176138 A2 | 7/1996 | ......... C07D/311/76 |
| WO | WO 01/07429 A1 | 6/2000 | ......... C07D/311/76 |

OTHER PUBLICATIONS

Napolitano, "The synthesis of isocoumarins over the last decade. A review." Organic Prep Procedures Int., 29:631–664, 1997.

Barry, "Isocoumarins. Developments since 1950," Chemical Reviews, 64:229–*260, 1964.

Mukhopadhyaya et al., "Synthesis of 6,8–dimethoxyisocoumarin," Indian Chem. J. 13:635–634, 1975.

Kita et al., "Enantioselective total synthesis of a potent antitumor antibiotic Fredericamycin A," J. Am. Chem. Soc., 123:3214–3222, 2001.

Shair et al., "The total synthesis of Dynemicin a leading to development of a fully contained bioreductively activated enediyne prodrug," J. Am. Chem. Soc., 118:9509–9525, 1996.

Tirodkar et al., "Isocoumarins: Part V—Synthesis of 3–methyl and 4–carboxy–3–methylisocoumarins," J. Indian Chem. Soc., 46:935–944, 1969.

Tirodkar et al., "Isocoumarins: Part VII—Synthesis of 3–ehtylisocoumarins and 4–carboxy–3–ehtylisocoumarins," Indian J. Chem., 9:123–125, 1970.

Tirodkar et al, "Isocoumarins: Part VIII—Synthesis of 6,7–dimethoxy–3–alkyl–isocoumarins," J. Indian Chem. Soc., 48:192–198, 1971.

(List continued on next page.)

Primary Examiner—Amelia Owens
(74) Attorney, Agent, or Firm—Stephen J. Moloney; Al A. Jecminek

(57) ABSTRACT

The present invention provides a process from preparing isocoumarin-3-yl derivatives comprising reacting a homophthalic anhydride derivative with a carbonyl compound, wherein the carbonyl group is substituted with an acyl activating group, in the presence of a reaction medium comprising a solvent and a base. The invention also encompasses a process for the preparation of homophthalate esters useful in the preparation of homophthalic anhydride reactants as well as an integrated process wherein the twp reactions are carried out sequentially to afford the desired isocoumarin derivative.

26 Claims, 3 Drawing Sheets

OTHER PUBLICATIONS

Langer et al., "Regioselective synthesis of functionalized homophathalates by cyclizations of 1,3–bis–(trimethlysiloxy)–1,3–butadienes with a–allenylesters," Tetrahedron Lett., 41:4545–4547, 2000.

Ayyangar et al., "Novel reactions: Part II—hologous condensations of phthalic and homophtalic anhydrides; 13C NMR and mechanism of formation of isocoumarins," Indian J. Chem., 22B:1108–1115, 1983.

Tamura et al., "Anthracyclinone syntheses using stron base induced cycloaddition of homophthalic anhydrides and related compounds," 22:4539–4548, 1984.

Henderson et al., "Synthesis of chlorinated isocoumarin derivatives," J. Chem. Soc. Perkin Trans. I, 1111–1115, 1982.

Bovicelli et al., "Selective halogenation of aromatics by dimethyl–dioxirane and halogen ions," Synthetic Commun., 31:2955–2963, 2001.

Carter et al., "Synthesis of isocoumarins vai indanones," J. Chem. Soc. Perkin Trans. I, 1438–1441, 1976.

Carter et al., "Synthesis of indan–1–ones and isocoumarins," J. Chem. Soc. Perkin Trans. I. 471–479, 1981.

Babin et al., "Une synthesis originale et inattendue d'isocoumarines functionnelles," Tetrahedron Lett., 25:4389–4392, 1984.

Razzuk et al., "The reaction of various methoxy–substituted haloarenes with amines and nitriles under aryne–forming conisitions," J. org. Chem., 1987.

Pini et al., "Regioselctivity ortho–alkylation of N,N–diethylbenzamides via lithation and copper transmethylation," J. Organometallic Chem., 452:C4–C5, 1993.

Carlsen et al., "A greatly improved procedure for ruthenium tetroxide catalyzed oxidations of organic compounds," J. Org. Chem. 46: 3936–3938, 1981.

Sinha et al., "sythesis of some new 3–ethyl and 3–phenyl-isocoumarins," Ind. J. Heterocyclic Chem. 1:235–240, 1992.

Abell et al., :The Wittig Reaction With glutaric and succinic anhydrides, Aust. J. Chem. 35:2287, 1982.

Bhakta, C. Indian J. Chem., Sect. B 1986, 25B, 189–190.

Matstuda, F.; Kawasaki, M.; Ohsaki, M.; Yamada, K.; Terashima, S. Chem. Lett. 1989, 653–656.

Matsuda, F.; Kawasaki, M.; Ohsaki, M.; Terashima, S. Tetrahedron 1988, 44, 5745–5760.

Seconi, G., Taddei, M.; Eaborn, C.; Stamper, J.G.F. chem. Soc., Perkin Trans 2 1982, 6, 643–646.

PROCESS FOR PREPARING ISOCOUMARINS

This application claims priority to U.S. Application serial No. 60/303,532, filed Jul. 6, 2001 and to U.S. Application serial No. 60/352,407, filed Jan. 28, 2002.

FIELD OF THE INVENTION

The present invention relates generally to the chemical preparation of isocoumarin compounds. More specifically, the invention relates to the conversion of homophthalic anhydrides to isocoumarins and the preparation of homophthalic acid intermediates. Isocoumarin derivatives are valuable compounds in the fields of angiogenesis inhibition, immuno-regulation, and cancer therapy.

BACKGROUND OF THE INVENTION

Isocoumarins have been synthesized by a number of different methods. These methodologies include, but are not limited to: oxidation of indenes, indanone and indenones; condensation via Stobbe condensation with aldehydes and ketones and Claisen condensation with formates and oxalates; cyclization of 2-carboxybenzyl ketones, 2-vinylbenzoic acids, α-cyanohomophthalic acids and 2-formylbenzoates; and reduction of phthalides. For reviews of isocoumarin synthesis, see Barry, Chemical Rev. 64:229–260, 1964; Napolitano, Org. Prep. Proced. Int. 29:631–664, 1997.

Homophthalic anhydrides have also been utilized in the synthesis of isocoumarin derivatives. 2-Carboxyphenylacetates can be prepared by methanolysis of homophthalic anhydrides. Lithium borohydride reduction of these half-esters yields 3,4-dihydroisocoumarins. (Bose & Chaudhury, Tetrahedron. 20:49–51, 1964). Condensation of homophthalic anhydride with hydroquinone in the presence of stanic chloride yields 2-(2,5-dihydroxyphenyl) isocoumarin (Sorrie & Thomson, J. Chem. Soc. 2244, 1955). Homophthalic anhydride adds to ferrocene to produce ferrocenylhomophthalic acid, which can be cyclized to 3-ferrocenylisocoumarin (Boichard, Compt. Rend. 253:2702, 1961). Further, Perkin condensation of homophthalic anhydrides with aromatic aldehydes in the presence of bases such as triphenylmethylsodium, yields 3-phenyl-3,4-dihydroisocoumarin-4-carboxylic acids (Jones & Pinder, J. Chem. Soc., 2612, 1958).

Methods for preparing isocoumarin-3-yl acetic acid derivatives are disclosed in WO0107429. In one process, a homophthalate monoester derivative is reacted with a malonic acid monoester salt in a suitable solvent in the presence of a condensing agent to form a β-oxocarboxylic acid derivative, which is subsequently cyclized in a suitable inert solvent, in the presence of a base. The reaction is as follows:

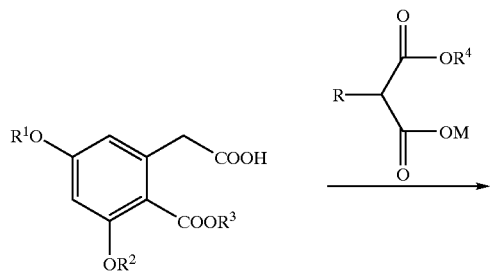

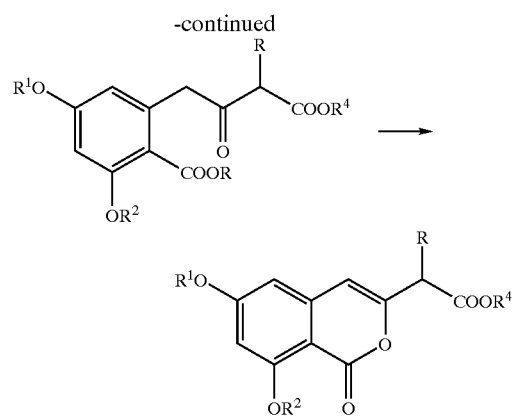

An alternative method of preparation of the same compound disclosed the reaction of a homophthalic acid derivative with a malonyl halide monoester in the presence of a base. One disadvantage of these methods is that the synthesis disclosed in WO0107429 for homophthalate esters has a low yield and provides an intermediate ester with free hydroxy groups that must be subsequently protected in a separate step.

The synthesis of 3-yl-isocoumarins is also disclosed by Tirodkar & Usgaonkar, J. Indian Chem Soc., 46, 1934–933, 1969; Tirodkar & Usgaonkar, Indian J. Chem, 9: 123–125, 1970; Tirodkar & Usgaonkar, J. Indian Chem Soc., 48:192–198, 1971; and Sinha et al, Indian J. Heterocyclic Chem., 1:235–240, 1992. These methods describe the formation of 4-carboxy-3-yl-isocoumarins by reaction of an anhydride with an isochroman-1,3-dione carbanion or enolate intermediate, formed from the corresponding homophthalate under basic conditions. Decarboxylation under acidic conditions or by heating resulted in the corresponding 3-yl-isocoumarin. This reaction is summarized in FIG. 1.

Despite the preparative methods for isocoumarins known in the art, there is still a need for economically preferable, effective and efficient process for the preparation of isocoumarin derivatives. The object of the present invention is to provide such a process. Further objects are to minimize the number of process reaction steps, to enhance overall yields of desired end products and to provide a process that is readily scalable for the production of commercial-scale quantities. Other objects and advantages will become apparent to persons skilled in the art and familiar with the background references from a careful reading of this specification.

SUMMARY OF THE INVENTION

In its most general terms, the present invention provides for the preparation of isocoumarin derivatives and intermediates useful in such preparative procedures. One aspect of the invention provides a process for preparing isocoumarin derivatives comprising reacting a homophthalic anhydride derivative with a carbonyl compound, wherein the carbonyl group is substituted with an acyl activating group, in the presence of a reaction medium comprising an inert solvent and a base. The inventors discovered this novel reaction results in the formation of isocoumarin derivatives in high yield and provides an efficient method of preparation of such compounds. Another aspect of the present invention is the preparation of homophthalate esters based on the discovery that, surprisingly, the addition of a malonate anion to a benzyne intermediate formed from a 2,4-disubtituted halobenzene, results in the selective production of a 3,5-disubstituted homophthalate ester. Such esters can be readily converted into the equivalent anhydride and are, thereby, useful in the preparation of isocoumarin derivatives according to the methods provided by the present invention In one aspect, the present invention provides a process for the preparation of the isocoumarin derivatives of formula (1):

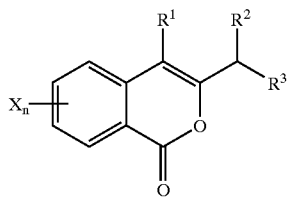

(1)

where $R^1$ and $R^2$ independently represent hydrogen, halogen, which may be chloro, bromo, iodo of fluoro, an aryl group, a heteroaryl group, or a $C_1-C_6$ alkyl, $C_1-C_6$ alkenyl, $C_1-C_6$ alkynyl, $C_1-C_6$ acyl, or $C_1-C_6$ alkoxy group. $R^1$ and $R^2$ further independently represent the substituted amino function —$NR^4R^5$, where either $R^4$ is hydrogen and $R^5$ is sulfonyl or $C_1-C_6$ acyl or where $R^4$ and $R^5$ are independently $C_1-C_6$ alkyl or $C_1-C_6$ acyl. In a preferred embodiment, $R^1$ is hydrogen. In another preferred embodiment, $R^2$ is methyl.

$R^3$ represents an electron withdrawing group. In preferred embodiments, $R^3$ is an electron withdrawing group selected from aryl, hetroaryl, sulfonate, phosphonate, cyano, —$CO_2R^7$, wherein $R^7$ is $C_1-C_6$ alkyl, or an acid halide —$COR^8$, wherein $R^8$ is a halogen, which may be chloro, bromo, iodo of fluoro. In a more preferred embodiment, $R^3$ is —$CO_2C_2H_5$. $R^3$ may also form a ring structure with $R^2$, wherein the ring structure incorporates an electron withdrawing element, such ring structures include anhydrides, lactones, oxo-cycloalkanes and cyclic amides, including lactams and lactims.

The substituents represented by X include halo, which may be fluoro, chloro, bromo or iodo, aryl, heteroaryl, $C_1-C_6$ alkyl, $C_1-C_6$ alkenyl, $C_1-C_6$ alkynyl, $C_1-C_6$ acyl, or $C_1-C_6$ alkoxyl, or —$NR^4R^5$, where $R^4$ and $R^5$ are as defined above. X further represents —$SO_2R^6$, where $R^6$ is $C_1-C_6$ alkyl or $C_1-C_6$ acyl. The subscript n is an integer from 0 to 4, with the caveat that when n is 2, 3 or 4, the X substituents may be the same or different. In a preferred embodiment, subscript n is 2 and X is the same and is —$OCH_3$. In a more preferred embodiment, the isocoumarin derivative is 2-(6,8-dimethoxy-1-oxo-1H-isochromen-3-yl)-propionic acid ethyl ester (2)

(2)

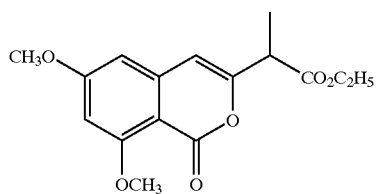

The process comprises reacting a homophthalic anhydride of formula (3):

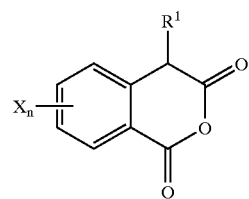

(3)

where $R^1$, X and subscript n are as defined above, with a carbonyl compound of formula (4):

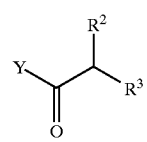

(4)

where $R^2$ and $R^3$ are as defined above, and Y is an acyl activating substituent. In preferred embodiments, Y is a halogen, pyridyl or aryloxy, and more preferably imidazoyl or chloro.

The reaction medium further comprises an inert solvent and a base. In certain embodiments, the solvent is an aprotic solvent such as a halogenated or ethereal solvent. In a preferred embodiment, the solvent is acetonitrile or N-methyl pyrrolidinone. In some embodiments of the present invention, the base can be a tertiary amine, amidine, amide or a tertiary alkoxide base. In preferred embodiments, the base is triethylamine, N,N-tetramethylguanidine or 1,8-diazabicyclo[5.4.0]-undec-7-ene.

In some embodiments of the present invention, 2-(6,8-dimethoxy-1-oxo-1H-isochromen-3-yl)-propionic acid ethyl ester (2), undergoes hydrolysis to remove the ethyl ester group and the methyl group at position 8 to produce 2-(8-hydroxy-6-methoxy-1-oxo-1H-isochromen-3-yl)-propionic acid (5), also known as NM-3, which is disclosed and claimed in U.S. Pat. No. 6,020,363, hereby incorporated by reference:

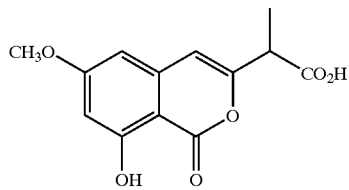

An alternative reaction to that with the carbonyl compound (4), is wherein the homophthalic anhydride (3) undergoes a self condensation to produce the isocoumarin derivatives depicted by compound (6):

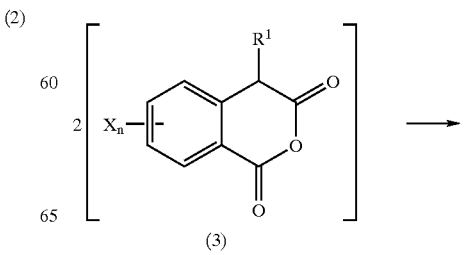

(3)

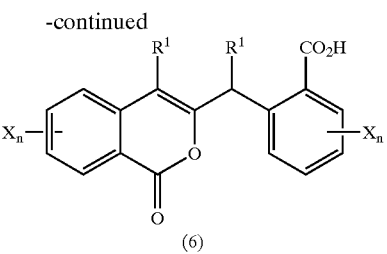

(6)

wherein $R^1$, X and n are as previously defined. The reaction is believed to proceed in a similar fashion to that of the compounds of formula (3) with the activated carbonyl compounds of formula (4). Thus, similar reactions conditions may be used to from the condensation products of formula (6).

Another aspect of the present invention is a process for the preparation of homophthalate derivatives of formula (7):

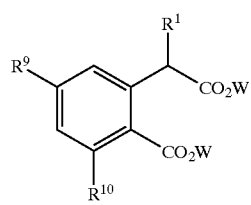

(7)

wherein W represents a carboxy protecting group, which in preferred embodiments is methyl or ethyl. $R^9$ and $R^{10}$ independently represent the substituents as described above for X. In preferred embodiments, $R^9$ and $R^{10}$ are independently $C_1$–$C_6$ alkyl or $C_1$–$C_6$ alkoxy. $R^1$ is as defined above, and in a preferred embodiment is hydrogen.

The process comprises reacting a 2,4-disubstituted or a 3,5-disubstituted halobenzene derivative of formula (8) or (9) respectively:

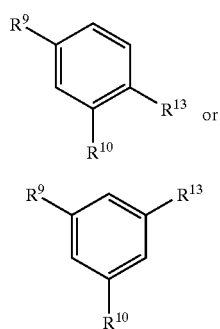

(8)

or (9)

where $R^9$ and $R^{10}$ are as defined above, and $R^{13}$ is a halogen, which, in some embodiments, is chloro, fluoro or bromo, a sulfonate ester or a leaving group such as tosylate or triflate; and a malonate ester of formula (10):

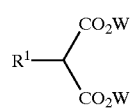

(10)

where W and $R^1$ are as defined above, and where in a preferred embodiment, $R^1$ is hydrogen, in the presence of a solvent and a strong base, for example a base with a pKa in water of about 30 or above. In a preferred embodiment, the solvent is tetrahydrofuran. In other preferred embodiments, the strong base is lithium diisopropylamide (LDA), lithium tetramethylpiperidide, lithium hydride or a mixture of bases such as LDA and sodium hydride or potassium hydride. In other preferred embodiments, $R^{13}$ is chloro or bromo.

In some embodiments, the malonate ester (10) is first reacted with a strong base to form a malonate ester salt (11):

(11)

wherein $M^+$ is a monovalent cation. The base may be alkali metal base, which may be sodium hydride or lithium hydride, wherein $M^+$ in the malonate salt (11) is $Na^+$ and $Li^+$ respectively. Either the 2,4-disubstituted halobenzene (8) or 3,5-disubstituted halobenzene (9) is then added with the optional addition of a second strong base, the addition of which can be either before or after the addition of the disubtituted halobenzene. In a preferred embodiment, the optional second strong base is added after the disubtituted halobenzene (8) or (9). In another preferred embodiment, the optional second strong base is LDA.

The process according to the present invention is highly selective in that the desired homophthalate derivative of formula (7) is produced in a molar ratio of at least about 7.0:3.0, or in a molar ratio of at least about 8.0:2.0, or in a molar ratio of at least about 9.0:1.0 in comparison to the homophthalate derivative of formula (12). In a preferred embodiment, the desired homophthalate (7) is produced substantially free of the positional isomer (12), that is, in a molar ratio of at least about 9.5:0.5 of (7):(12). In another preferred embodiment, there is no detectable level of the homophthalate derivative of formula (12) produced during the reaction of a disubstituted halobenzene derivative of formula (8) or formula (9) and a malonate ester of formula (10), as measured by HPLC and U.V. analyses.

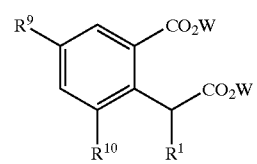

(12)

The process further comprises embodiments wherein the carboxy protecting groups W are removed to form the homophthalic acid derivative of formula (13):

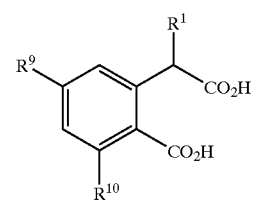

(13)

In some embodiments, the homophthalic acids of formula (13) undergo dehydration to form the homophthalic anhydrides of formula (14):

(14)

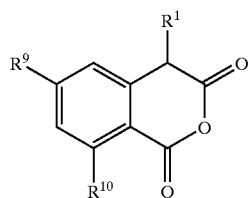

wherein $R^1$, $R^9$ and $R^{10}$ are as defined above.

The process of the invention also further comprises reacting the anhydride of formula (14) with a carbonyl compound of formula (4), wherein the reaction medium comprises a solvent and a base to afford the derivatized isocoumarin product. In some embodiments, the carbonyl compound of formula (4) is the carbonyl compound of formula (15):

(15)

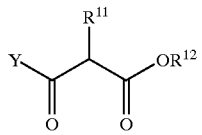

wherein $R^{11}$ and $R^{12}$ are independently $C_1$–$C_6$ alkyl, and Y is an acyl activating group. In a preferred embodiment, the reaction of the anhydride of formula (14) wherein $R^1$ is hydrogen, with the carbonyl compound of formula (15) results in the formation of the isocoumarin derivative of formula (16):

(16)

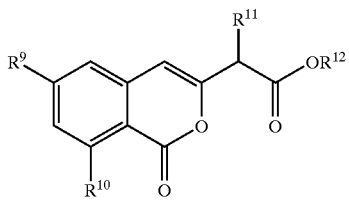

In a preferred embodiment, where $R^9$ and $R^{10}$ are methoxy, $R^{11}$ is methyl and $R^{12}$ is ethyl, the reaction process of the present invention provides the isocoumarin derivative 2-(6,8-dimethoxy-1-oxo-1H-isochromen-3-yl)-propionic acid ethyl ester (2). In another preferred embodiment, the process further comprises removal of the ethyl ester group and the methyl group at position 8 of 2-(6,8-dimethoxy-1-oxo-1H-isochromen-3-yl)-propionic acid ethyl ester (2) to provide 2-(8-hydroxy-6-methoxy-1-oxo-1H-isochromen-3-yl)-propionic acid (5).

Also within the scope of the invention is an integrated stepwise process wherein isocoumarins of formula (1) are prepared starting from a substituted halo-benzene of formula (8) or formula (9) which is reacted with a malonate ester of formula (10) to afford a homophthalate derivative of formula (7), which in turn, after optional deprotection/dehydrations, is reacted with a carbonyl compound of formula (4) to afford the desired isocoumarin derivatives.

DETAILED DESCRIPTION OF THE INVENTION

1. Preparation of Isocoumarins from Homophthalate Anhydride Derivatives

The present invention provides a process for preparing isocoumarin compounds by using a homophthalate anhydride as the nucleophilic component in a reaction with a suitable electrophile. Thus the reaction can be depicted as follows, wherein all substituents are as previously defined:

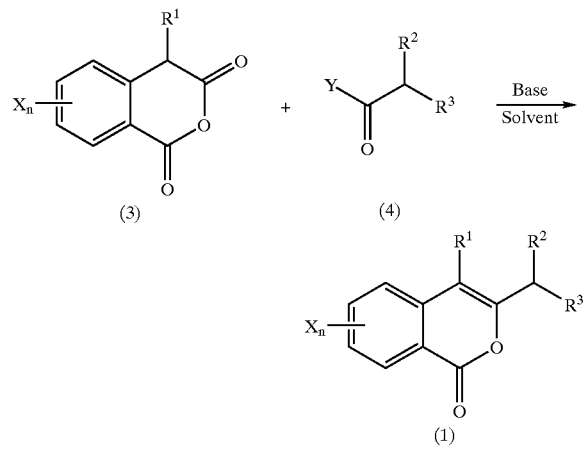

Figure 1:
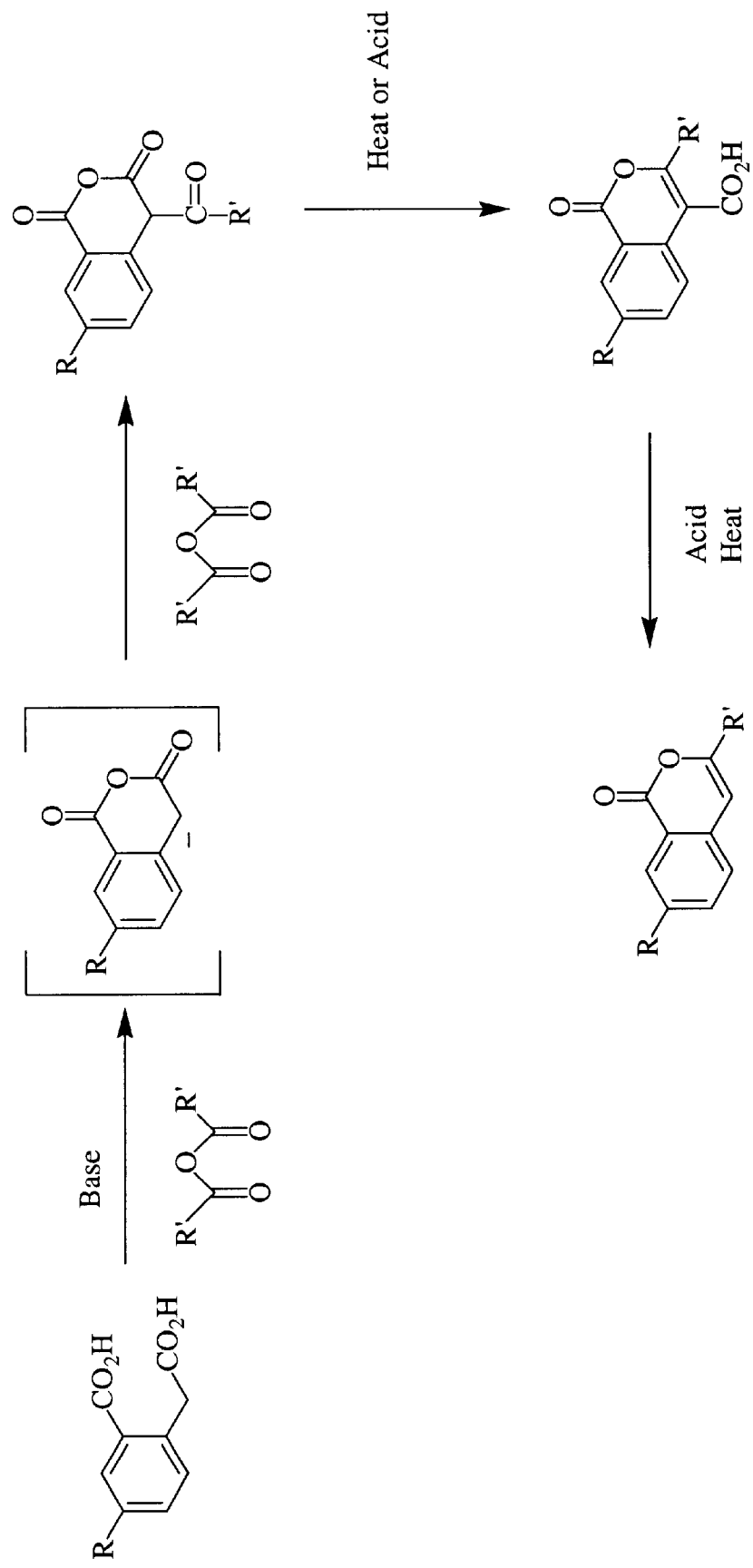
FIG. 1: Summary of isocoumarin syntheses as per Tirodkar & Usgaonkar, J. Indian Chem Soc., 46, 1934–933, 1969; Tirodkar & Usgaonkar, Indian J. Chem, 9: 123–125 1970; Tirodkar & Usgaonkar, J. Indian Chem Soc., 48:192–198, 1971; and Sinha et al, Indian J. Heterocyclic Chem., 1:235–240, 1992. R is H or methoxy and R' is alkyl or aryl.
Figure 2:
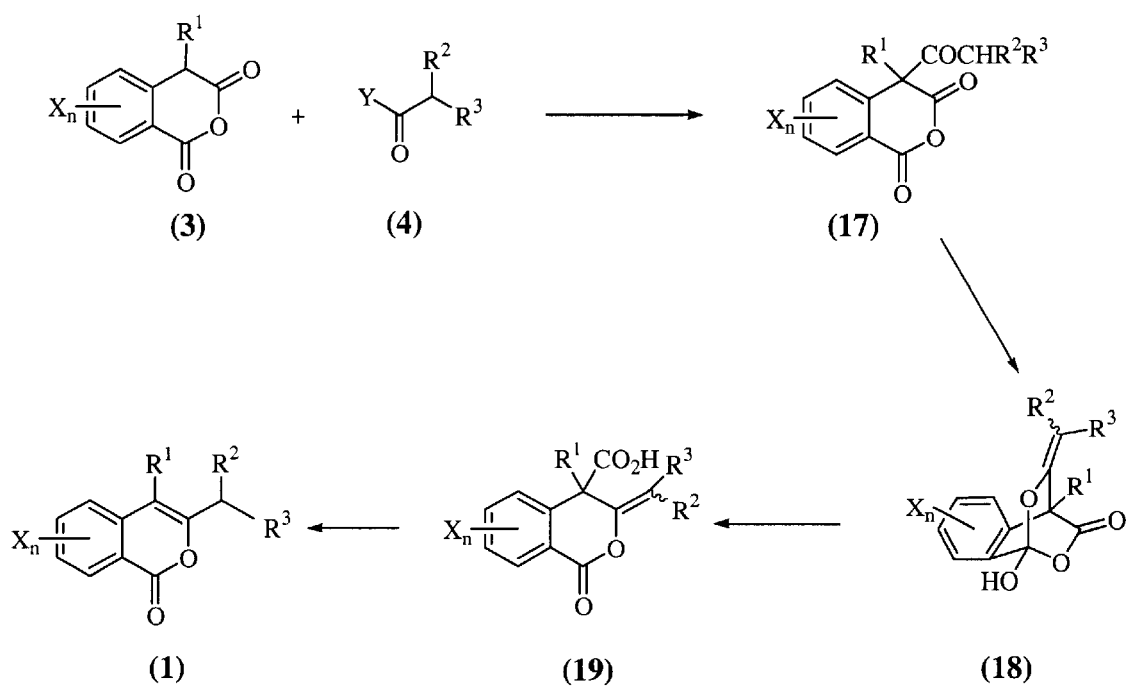
FIG. 2: Summary of proposed mechanism of reaction of the present invention.

Without being bound by any particular theory, it is presently believed that the mechanism for the reaction of the present invention is shown in FIG. 2. The initial acylation forms the novel compound (17) which rearranges to the dioxabicyclo[2,2,2]-octene skeleton of compound (18). The ortho ester function then opens under basic conditions to give compound (19), which readily decarboxylates. The resulting extended enolate is then thermodynamically protonated at the exocylic methane carbon to afford the isocoumarin compound (1).

The molar ratio of compound (4) to (3) to be reacted is not considered to be critical and is preferably in the range of about 1.0 to about 1.5. The molar ratio of base to other reactants is also not critical, and typical molar ratios of base to the homophthalic anhydride of formula (3) are in the range of about 1.0 to about 1.5. and are preferably about 1.0 to about 1.2.

The Y substituent is an acyl activating group. The term "acyl activating group" refers to a substituent to a carbonyl that promotes nucleophilic addition reactions to the carbonyl. Suitable activating substituents are those which have a net electron withdrawing effect on the carbonyl. For example, a halogen attached to carbonyl (i.e., acyl halides) activates the carbonyl for nucleophilic addition. Suitable halogens include chloro, bromo, or iodo. Other typical electron withdrawing groups include groups that when combined with the carbonyl form an ester or amide. Such groups include hydroxybenzotriazole, imidazole, a nitrophenol, including 4-nitrophenoxy and 2-nitrophenoxy, pentachlorophenoxy, pentafluorophenoxy, N-hydroxysuccinimide, dicyclohexylcarbodiimide, N-hydroxy-N-methoxyamine, 3-hydroxy-3,4-dihydro-4-oxo-benztriazine, 1-hydroxybenztriazole, 1-hydroxy-7-azabenzotriazole, aryloxy, pyridyl, and the like. Other acyl-activating groups include acyloxy, acylisourea and acylazide.

The $R^3$ substituent is an electron withdrawing group, which thus also encompasses the compounds represented by the Y substituent. The $R^3$ substituent may be an aryl or heteroaryl group, wherein the electron withdrawing properties of the group may be due to the inductive effect of the aryl or heteroaryl ring system and/or by substituents if present. $R^3$ may also form a ring structure with $R^2$, wherein the ring structure incorporates an electron withdrawing element. Examples include anhydrides, such as when the ring formed by linking $R^3$ and $R^2$ is equivalent to glutaric anhydride or succinic anhdride, lactones, oxo-cylcoalkanes, such as oxo-pentane, oxo-cyclohexane, oxo-cycloheptane, and oxo-cyclooctane, preferably when the carbon with the oxo-substituent is beta to isocoumarin nucleus, and cyclic amides, such as lactams and lactims. Wherein $R^3$ is a phosphonate, the term phosphonate encompasses the free acid and esters, such esters to include alkyl esters, e.g., methyl, ethyl, n-propyl, isopropyl and t-butyl esters.

When used herein, the term alkyl, alkenyl, alkynyl, acyl and alkoxy include halogenated alkyl, alkenyl, alkynyl, acyl and alkoxy groups. Such halogenated groups to include fluoro alkyl, alkenyl, alkynyl, acyl and alkoxy groups, wherein the degree of fluoro substitution ranges from one fluoro to perfluoro alkyl, alkenyl, alkynyl, acyl and alkoxy groups.

When used herein, the term "aryl" refers to an unsaturated aromatic carbocyclic group of from 6 to 14 carbon atoms having a single ring (e.g., phenyl) or multiple condensed rings (e.g., naphthyl or anthryl). The aryl groups may be optionally substituted, wherein such substituents include halo, akyl, akenyl, alkoxy, acyl, acylamino, acyloxy, amidino, amino, nitro, aryl or heteroaryl.

When used herein the term "heteroaryl" refers to, unless otherwise defined, a single or a fused ring containing up to four heteroatoms in each ring, each of which is selected from oxygen, nitrogen and sulphur, which rings, may be unsubstituted or substituted by, for example, up to four substituents. Each ring suitably has from 4 to 7, preferably 5 or 6 ring atoms. A fused ring system may include carbocyclic rings and need include only one heteroaryl ring.

Representative examples of heteroaryl groups include pyridyl, pyrimidyl, pyrazinyl, pyridazinyl, thiaphene, thiazolyl, thiadiazolyl, benzothiazolyl, isoxazolyl, pyrazolyl, triazinyl, and imidazolyl which may be unsubstituted or substituted by up to four substituents (for pyridyl and benzothiazolyl), three substituents (thiophene, pyrimidyl, pyrazinyl, pyridazinyl, pyrazolyl), two substituents (thiazolyl, isoxazolyl, triazinyl and imidazolyl) or one substituent (thiadiazolyl) which may be the same or different and include halo, haloalkyl, akyl, akenyl, alkoxy, acyl, acylamino, acyloxy, amidino, amino, nitro, aryl or heteroaryl.

In one aspect of the invention, the solvent used in the reaction mixture is an aprotic solvent, which is a solvent that neither yields nor accepts a proton. Aprotic solvents include non-halogenated and halogenated aromatic and aliphatic hydrocarbons, such as xylenes, toluene, dichloromethane and the like. Aprotic solvents also include ethereal solvents such as tetrahydrofuran, and further include tertiary amines, pyridine and hindered pyridines such as lutidine, collidine, and picoline. Other aprotic solvents include, but are not limited to, acetonitrile, propylene carbonate, sulfolane (tetramethylene sulfone), N,N-dimethylformamide, N,N-dimethyacetmide, N-methylpyrollidone, dimethylsulfone, dimethylsulfoxide, triglyme (triethylene glycol dimethyl ether), N-methylpyrrolidinone, benzonitrile, hexamethylphosphoramide, toluene, dioxane or mixtures of two or more of such materials.

Various bases may be used in the present invention, including amidine bases such as 1,5-diazabicyclo[4.3.0]-non-5-ene or 1,8-diazabicyclo[5.4.0]undec-7-ene. Other bases include organic amine base like triethylamine, diethylamine, diethyl isopropylamine, DABCO or related di- or trialkylamines. Tertiary alkoxide bases include alkaline metal alkoxides such as the potassium, sodium and lithium salts of tert-butoxide and tertamylate. Hindered bases include bases such as lithium diisopropylamide, lithium bis(trimethylsilyl)amide, lithium tetramethylpiperidide, lithium, sodium or potassium hexamethyldisilazide, N,N,N',N'-tetramethylguanidine (TMG) and the like. When the Y substituent of compound (4) is a halide, it is preferred to use a strong base with a pKa in the range of 11–13.6, such bases including DBU and TMG, optionally in combination with a weaker base such as triethylamine ("TEA"). In some embodiments, the strong base is added to the anhydride (3) with the subsequent addition of compound (4) wherein Y is a halide, with a second base. In a preferred embodiment, the second base is triethylamine. Use of TMG requires that the tertiary amine base is added prior to the addition of the acyl chloride prevent acylation of the TMG.

In typical embodiments, the reaction is suitably conducted at a temperature of about room temperature or at a temperature up to the boiling point of the reaction solvent mixture wherein the reaction mixture is refluxed. Such temperatures employed may be about 20° C., or about 30° C., or about 40° C., or about 50° C., or about 60° C., or about 70° C.

The preferred order and manner of addition for any specific embodiment can be determined by routine experimentation with a view towards both reaction performance and chemical engineering and production considerations. In a preferred embodiment, the anhydride (3) is added slowly to the reaction mixture.

The present invention also encompasses the removal of hydroxyl and carboxyl protection groups when desirable from isocoumarin derivatives encompassed by formula (1). For example, the methyl group from the 8-methoxy substituent may be removed from 2-(6,8-dimethoxy-1-oxo-1H-isochromen-3-yl)-propionic acid ethyl ester (2), as disclosed in WO0107429, hereby incorporated by reference. Deprotecting the 8-position can be achieved by use of an alkaline metal iodide (e.g., potassium or sodium iodide) and a magnesium halide, preferably magnesium chloride, in an inert solvent (e.g., tetrahydrofuran, dioxane or acetonitrile) at 20 to 100° C., and preferably 60 to 80° C. Subsequent removal of the ethyl ester function of the 8-hydroxy derivative of the compound of formula (2), thereby producing 2-(8-hydroxy-6-methoxy-1-oxo-1H-isochromen-3-yl)-propionic acid (5), can be achieved by hydrolytic reactions well known in the art. Removal of protecting groups from other isocoumarin compounds of the present invention can be achieved by routine experimentation utilizing methodologies and procedures know in the art.

2. Preparation of 3,5-Dialkoxy Substituted Homophthalates and Corresponding Anhydrides Homophthalate anhydrides as represented by formula (3), used in the present invention for the preparation of isocoumarin derivates, are suitably prepared from the corresponding homophthalic acid derivatives (20):

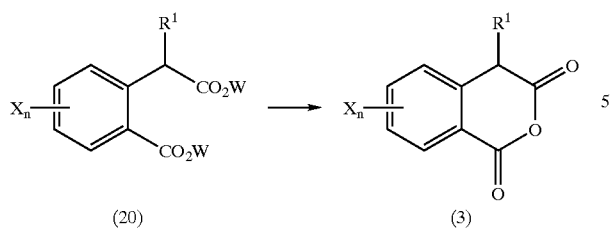

(20)     (3)

Wherein $X_n$ and $R^1$ are as previously defined and W represents a carboxyl protecting group. The homophthalic acid derivatives of formula (20) can be prepared by several methods. WO0107429, herein incorporated by reference, discloses the preparation of 3,5-disubstitued homophthalates by reacting an acetonedicarboxylic acid ester with a diketene. Other methods include cycloaddition of allenyl esters to dienes (Tamura et al., Chem. Pharm. Bull. 32:3259–3262, 1984; Roush et al., J. Org. Chem. 57:6622–6629, 1992; Langer et al., Tetrahedron Lett. 41:4545–4547, 2000, all herein incorporated by reference) and ortho-lithiation of benzoic acid derivatives (Cushman and Dekow, Tetrahedron 34:1435–1439, 1978; DeSilva et al., Can. J. Chem. 57:1598–1605, 1979; Tamura et al., Tetrahedron 40:4539–4548, 1984, all herein incorporated by reference). A further method is the addition of malonate anions of formula (22) to the benzynes of formula (21) (Shair et al, J. Am. Chem. Soc. 118:9509–9525, 1996; Kita et al., J. Am. Chem. Soc. 123, 3214–3222, 2001, both herein incorporated by reference). The latter method results in the two isomers of formulas (20) and (23):

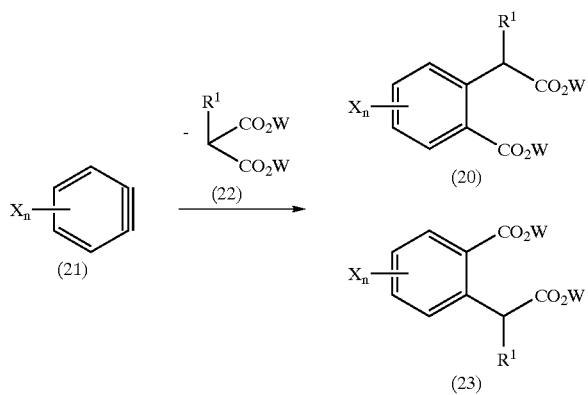

One aspect of the present invention encompasses the utilization of this method in the surprising selective production of a 3,5-dialkoxy substituted homophthalate isomer. The product ester is believed to arise through a benzyne intermediate that is formed in situ. In this aspect of the invention, the benzyne intermediate is formed by reaction of a strong base, for example a base with a pKa in water of about 30 or above, with a 2,4-substituted or 3,5-disubstituted halobenzene of formulas (8) and (9) respectively:

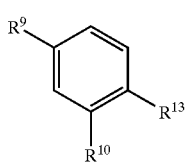

(8)

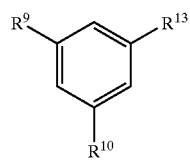

(9)

wherein $R^9$ and $R^{10}$ are as defined above and $R^{13}$ is a halogen, which may be bromo, chloro, iodo or fluoro, or a sulfonate ester or a leaving group such as tosylate or triflate. Examples of suitable strong bases are lithium, sodium and potassium hydrides and lithium, sodium and potassium secondary amides. The secondary amine may be a dialkylamide, e.g., diethylamide, diisopropylamide, ditertiarybutylamide, dicyclohexylamide, t-butyl-cyclohexylamide, N-t-amyl-N-t-butylamide, N-isopropyl-N-cyclohexylamide or N-(1'-ethylcyclohexyl)-1,1,3,3-tetramethylbutylamide or a cyclic compound, e.g., piperidine or 2,2,6,6-tetramethylpiperidine. In preferred embodiments the strong base is lithium diisopropylamide, lithium tetramethylpiperidide, lithium hydride or sodium hydride. Such strong bases may also be formed in situ by addition, typically at low temperature such as −60° C. to −70° C., of n-butyl lithium and the respective free bases, e.g., diisopropylamine or tetramethylpiperidine in a suitable solvent. In a preferred embodiment, the solvent is tetrahydrofuran. Other solvents may include 2-methyltetrahydrofuran, diethylether, diisopropylether, tert-butylmethyl ether, dioxane, or hexanes. In another embodiment the base is a hydride, such as potassium or sodium hydride, wherein a cation complexing agent such as 1,4,7,10,13,16-hexaocyclooctadecane ("18-crown-6") or other crown ether may optionally be added. The formation of benzyne intermediates by interacting aryl halides with strong bases is disclosed in U.S. Pat. No. 4,296,029 and Shair et al, J. Am. Chem Soc. 118:9509–9522, 1996, both herein incorporated by reference.

The benzyne intermediate thus formed reacts with a malonate ester anion of formula (22), wherein W represents a carboxy protecting group. This reaction typically proceeds a low temperature, which may be about 10° C. to about −80° C., and may be about 5° C., about −10° C., or about −20° C., or about −30° C., or about −40° C. In some embodiments of the present invention, higher temperatures, including room temperature, are used. In some embodiments the malonate anion is first formed by reacting the malonate ester (10) with a strong base to form the malonate salt (11). Suitable strong bases include alkali metal bases, for example lithium, sodium and potassium hydride and strong amide bases such as LDA and lithium 2,2,6,6-tetramethylpiperidiide (LiTMP). The 2,4-substituted halobenzene (8) or 3,5-disubstituted halobenzene (9) is then added to the reaction. An optional second strong base may also be added before or after the halobenze (8) or (9). A preferred optional strong base is LDA. A preferred method is to add the second optional strong base slowly after the halobenze (8) or (9), thereby slowly forming the benzene intermediate.

As used herein, the term "carboxy protecting group" refers to a carboxylic acid protecting ester group employed to block or protect the carboxylic acid functionality while the reactions involving other functional sites of the compound are carried out. Examples of carboxy protecting groups include straight or branched chain ($C_{1-12}$)alkyl groups (e.g., methyl, isopropyl, t-butyl); lower alkoxy lower alkyl groups (e.g., methoxymethyl, ethoxymethyl, isobutoxymethyl); lower aliphatic acyloxy lower alkyl groups (e.g. acetoxymethyl, propionyloxymethyl, butyryloxymethyl, pivaloyloxymethyl); lower alkoxycarbonyloxy lower alkyl groups (e.g., 1-methoxycarbonyloxyethyl, 1-ethoxycarbonyloxyethyl); aryl lower alkyl groups (e.g., benzyl, p-methoxybenzyl, o-nitrobenzyl, p-nitrobenzyl, benzhydryl and phthalidyl); tri(lower alkyl)silyl groups (e.g., trimethylsilyl and t-butyldimethylsilyl); tri(lower alkyl)silyl lower alkyl groups (e.g., trimethylsilylethyl); and ($C_{2-6}$) alkenyl groups (e.g., allyl and vinylethyl). The species of carboxy-protecting group employed is not critical so long as the derivatized carboxylic acid is stable to the conditions of subsequent reaction(s) and can be removed at the appropriate point without disrupting the remainder of the molecule.

Methods particularly appropriate for the removal of carboxyl protecting groups are well known in the art and include for example acid-, base- and metal-catalyzed hydrolysis. Methods of dehydrating homophthalic acid derivatives to form anhydrides are known in the art and include use of trimethylsilyl(ethoxy)acetylene (Kita et al., J Org. Chem., 51: 4150–4158, 1986, herein incorporated by reference) and use of acetic anhydride, e.g., as exemplified in Example 5. The anhydrides thus formed by this aspect of the present invention, are useful as reactants in the aspect of present invention relating to the preparation of isocoumarin derivatives, as described above in Section 1.

EXAMPLES OF THE INVENTION

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Example 1

2-(6,8-dimethoxy-1-oxo-1H-isochromen-3-yl)-propionic Acid Ethyl Ester (2)

Milwaukee, Wis.), 0.291 g in 3 mL acetonitrile, was added via syringe over 10 minutes. Triethylamine ("TEA," Aldrich, Milwaukee, Wis.), 0.25 mL, was added to the solution over 30 sec. 6,8-Dimethoxy-isochroman-1,3-dione (25), 0.200 g in 4 ml acetonitrile, was added via syringe over 15 minutes at ambient temperature. The reaction mixture was stirred at ambient temperature for 5 hours and several aliquots were taken for in-process controls. Samples were analyzed by reverse-phase HPLC using a C18 5µ column (Phenomenex) and a mobile phase of 1:1 acetonitrile and water at a flow rate of 1 ml/min. Typical retention times are: imidazole (26) 2.3 min; anhydride (25) 4.4 min; dimer isocoumarin (27) 5.3 min; and isocoumarin (2) 7.5 min. Quantification was by calculation of peak area of UV detection at 244 nm. A byproduct, identified by NMR and mass spectrometry as the self-condensation product of the anhydride (27) was formed during this reaction.

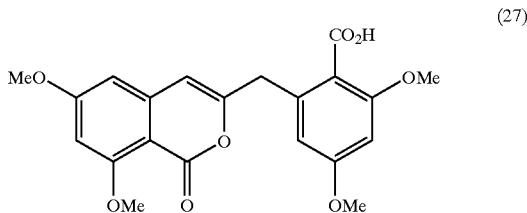

(27)

Consumption of the anhydride (25) and production of isocoumarin (2) and dimer (27) with time are shown in Table 1.

TABLE 1

| | Time | Anhydride (25) | Isocoumarin (2) | Dimer (27) |
|---|---|---|---|---|
| Start | 0.0 hr | 90.6% | 8.9% | 0.5% |
| | 1.0 hr | 70.8% | 19.9% | 9.3% |
| | 2.5 hr | 54.0% | 28.8% | 17.2% |

A. Synthesis Route I

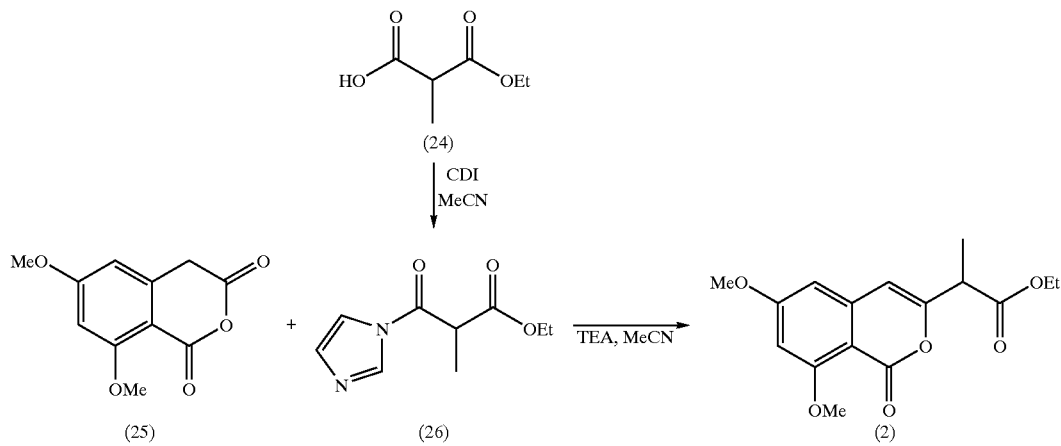

An oven dried, 25 mL, 3 neck flask, equipped with a magnetic stir bar under $N_2$ purge was charged with 0.200 g of ethyl-2-methyl malonate (24) at ambient temperature. Acetonitrile ("MeCN," Aldrich, Milwaukee, Wis.), 10 mL, was added via syringe over 1 minute to the stirring solid anhydride. Carbonyl diimidazole ("CDI," Aldrich, TABLE 1-continued

| Time | | Anhydride (25) | Isocoumarin (2) | Dimer (27) |
|---|---|---|---|---|
| | 4.0 hr | 11.4% | 72.5% | 16.1% |
| | 5.0 hr | 10.0% | 74.6% | 15.3% |
| End | 21.5 hr | 2.0% | 80.1% | 17.9% |

The solution was warmed in oil bath at between 50–60° C. for about 3.5 hr. Analyses of an in-process control aliquant taken at end of the time period indicated 89.0% isocoumarin (2) and 11.0% dimer (27). The solvent was removed on a rotary evaporator to give an orange oil. The crude oil was dissolved in ethyl acetate. The solution was washed with 1N HCl and the wet organic layer was dried over MgSO$_4$. The solvent was removed in vacuo. NMR revealed presence of dimer (27) byproduct. The crude oil was redissolved in ethyl acetate (10 ml) and the solution was washed twice with sat. NaHCO$_3$ (3 ml). The solution was dried over MgSO$_4$ and solvent removed to give isocoumarin (2) as an orange oil. NMR analysis indicated no detectable level of dimer (27). Crystals of isocoumarin (2) formed on standing. Designations assigned to NMR analysis of the isocoumarin of formula (2) are as follows:

$^1$HNMR (250 MHz) in CDCl$_3$

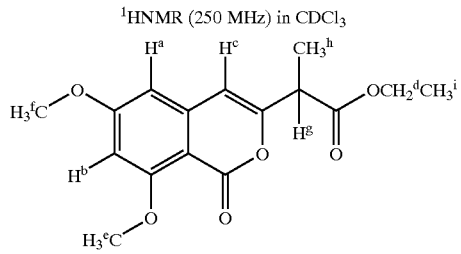

Proton a, 6.45 ppm (doublet, J=2.3 Hz, 1H); proton b, 6.37 ppm (doublet, J=2.3 Hz, 1H); proton c, 6.25 ppm (singlet, 2H); proton d, 4.18 ppm (quartet, J=7.2 Hz, 2H); proton e, 3.96 ppm (singlet, 3H); proton f, 3.89 ppm (singlet, 3H); proton g, 3.55 ppm (quartet, J=7.3 Hz, 1H); proton h, 1.51 ppm (doublet, J=7.3 Hz, 3 H); proton I, 1.25 ppm (triplet, J=7.2 Hz, 3H).

$^{13}$CNMR (62.5 MHz) in CDCl$_3$

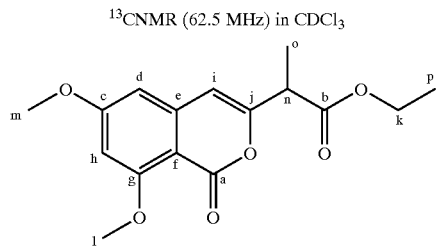

Carbon a, 171.4 ppm, carbon b, 158.7 ppm, carbon c, 165.3 ppm; carbon d, 103.6 ppm; carbon e, 141.6 ppm; carbon f, 103.1 ppm; carbon g, 163.1 ppm; carbon h, 98.6 ppm; carbon I, 100.1 ppm, carbon j, 156.1 ppm; carbon k, 61.3 ppm; carbon 1, 55.5 or 56.2 ppm; carbon m, 55.5 or 56.2 ppm; carbon n, 43.6 ppm; carbon o, 15.0 ppm; carbon p, 14.0 ppm.

B. Synthesis Route II

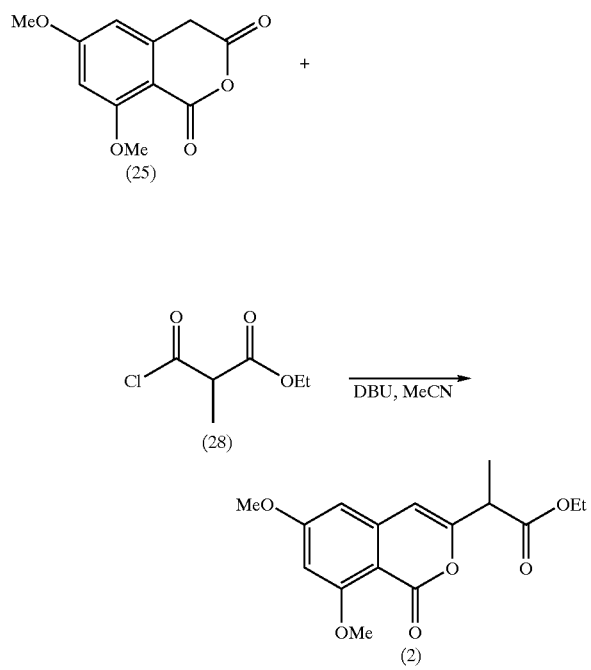

An oven dried 25-mL 3-neck round bottomed flask, equipped with a nitrogen inlet, magnetic stirring bar, and rubber septum, was charged with acetonitrile (5.0 mL) and 1,8-diazabicyclo[5.4.0]-undec-7-ene ("DBU") (0.3 mL) with stirring. 6,8-Dimethoxy-isochroman-1,3-dione (25) (222.2mg) dissolved in acetonitrile (5.0 mL) was added to the stirring solution by syringe pump over a 48 minute period at ambient temperature. The acid chloride of formula (28) (246.9 mg) was added by syringe over 4 minutes and then stirred an additional 10 minutes. An in-process control sample showed 96.5% conversion to the isocoumarin (2) as measured by reverse-phase BPLC using a C18, 5$\mu$ column (Phenomenex Luma) and a mobile phase of 1:1 acetonitrile-water. An additional 5 drops of the acid chloride (27) was added and the solution stirred for 10 minutes. Analysis of an in-process control sample indicated 96.6% conversion. The reaction was stirred for 17 hrs at ambient temperature resulting in a 99.9% conversion.

The solution was stripped of solvent to yield a reddish-brown oil that was then dissolved in 10 mL ethyl acetate and 10 mL of 1.0 N HCl. The layers were split and the organic layer was washed with 5 mL of 1.0 N HCl. The combined acidic layers were back-extracted with 5 mL ethyl acetate. The combined organic extracts were combined and washed twice with saturated NaHCO$_3$ and once with saturated NaCl. The solution was dried over MgSO$_4$ and the solvent removed in vacuo to give 240.3 mg of 2-(6,8-dimethoxy-1-oxo-1H-isochromen-3-yl)-propionic acid ethyl ester (2) as an orange oil (purity 89.9% a.u.c).

C. Synthesis Route III

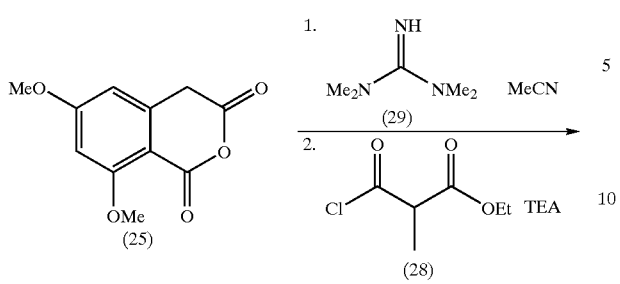

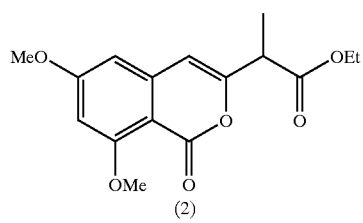

An oven dried 25 mL 3-neck flask, equipped with a nitrogen inlet, magnetic stir bar, and a rubber septum, was charged with 10 mL acetonitrile and TMG (29) with stirring. The solution was cooled to −20° C. and (25) in acetonitrile (6 mL) was added over 24 minutes via syringe pump maintaining an internal temperature of −20° C. TEA (0.28mL) was added in one portion. The acid chloride (28) was added by syringe over 3 minutes and then stirred an additional 20 minutes. The cooling bath was removed and the reaction allowed to warm to ambient temperature and then stirred approximately 18 hours at ambient temperature. The reaction was poured into 0.1N HCl (25 mL) and ethyl acetate (25 mL) and the phases were separated. The organic layer was washed twice with saturated NaHCO₃ (25 mL) and the combined aqueous layers were back-extracted with ethyl acetate (10 mL). The organic layers were washed with brine (25 mL) and then dried over MgSO₄ prior to removal of the solvent in vacuo to give the isocoumarin (2) (242 mg, 79% yield) as an orange oil (purity 95.7% a.u.c.).

Example 2

(6,8-Dimethoxy-1-oxo-1H-isochromen-3-yl)-acetic Acid Ethyl Ester (31)

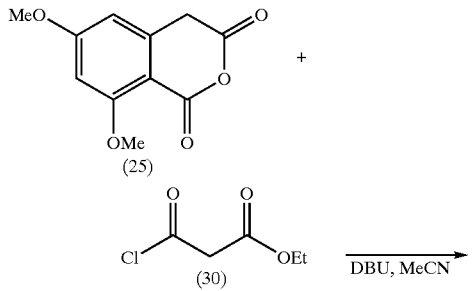

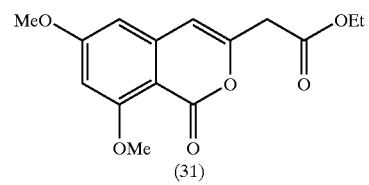

An oven dried 25-mL 3-neck round bottomed flask, equipped with a nitrogen inlet, magnetic stirring bar, and rubber septum, was charged with acetonitrile (5.0 mL) and 1,8-diazabicyclo[5.4.0]-undec-7-ene ("DBU") (0.3 mL) with stirring. 6,8-Dimethoxy-isochroman-1,3-dione (25) (222.19 mg) dissolved in acetonitrile (5.0 mL) was added to the stirring solution by syringe pump over a 54 minute period at ambient temperature. The acid chloride of formula (30) (0.19 mL) was added by syringe over 5 minutes and then stirred an additional 7 minutes. An in-process control sample showed 85% conversion to the isocoumarin (31) as measured by reverse-phase HPLC using a C18, 51μ column (Phenomenex Luma) and a mobile phase of 1:1 acetonitrile-water. An additional 68 minutes of stirring resulted in an increase to 87% conversion. An additional amount of the acid chloride (30) (30 μl) was added and the solution stirred overnight at ambient temperature resulting in a 94% conversion. Additional DBU was added (70 μl) and stirred for 2.6 hr resulting in 99% conversion.

The solution was diluted with 20 mL of ethyl acetate and washed with 20 mL of water. Toluene was added to the organic fraction and azodried. A solid formed which was slurried in CDCL₃ and then filtered through Na₂SO₄ and cotton. Solvent was removed to afford 246.8 mg of (6,8-dimethoxy-1-oxo-1H-isochromen-3-yl)-acetic acid ethyl ester (31) as an orange oil which solidified upon standing (purity 84.5% a.u.c.). Designations assigned to NMR analysis of the isocoumarin of formula (31) are as follows:

¹HNMR (250 MHz) in CDCl₃

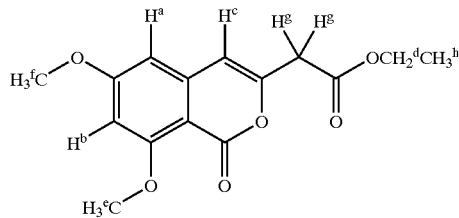

Proton a, 6.46 ppm (doublet, J=2.3 Hz, 1H); proton b, 6.36 ppm (doublet, J=2.3 Hz, 1H); proton c, 6.30 ppm (singlet, 2H); proton d, 4.20 ppm (quartet, J=7.2 Hz, 2H); proton e, 3.96 ppm (singlet, 3 H); proton f, 3.89 ppm (singlet, 3H); proton g, 3.55 ppm (quartet, J=7.3 Hz, 1H); proton h, 1.27 ppm (triplet, J=7.2 Hz, 3H).

Example 3

2-(6,8-Dimethoxy-1-oxo-1H-isochromen-3-yl)-cyanomethane (32)

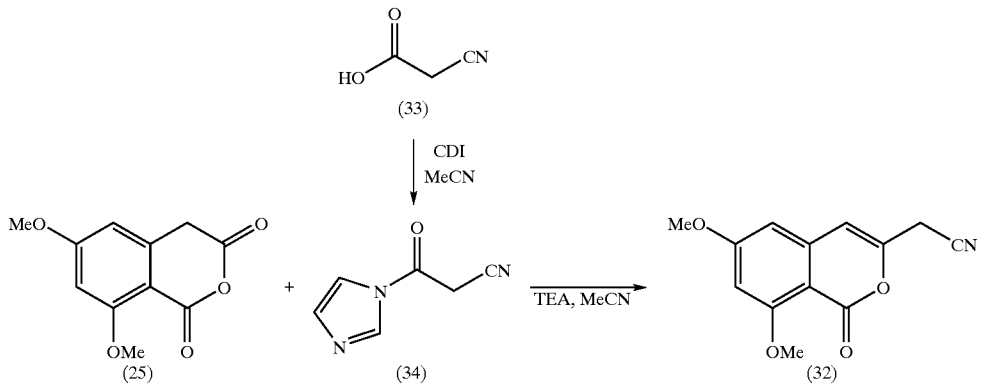

An oven dried, 25 mL, 3 neck flask, equipped with a magnetic stir bar under $N_2$ purge was charged with 0.474 g of cyanoacetic acid (Acros Organics) (33) at ambient temperature. Acetonitrile ("MeCN," Aldrich, Milwaukee, Wis.), 10 mL, was added to give a clear solution to which carbonyl diimidazole ("CDI," Aldrich, Milwaukee, Wis.), 0.908 g in 10 mL acetonitrile, was added. Triethylamine ("TEA," Aldrich, Milwaukee, Wis.), 0.78 mL, was added to the solution over 30 sec. 6,8-Dimethoxy-isochroman-1,3-dione (25), 0.629 g in 10 ml acetonitrile, was added via syringe over 11 minutes at ambient temperature. The reaction mixture was stirred at ambient temperature for approximately 22 hours and the solvent removed from the mixture producing a yellow solid. The solid was partitioned between ethyl acetate (50 mL) and 0.5N HCl (40 mL) and the organic phase was washed first with water (40 mL) and then twice with ½saturated $NaHCO_3$ (40 mL). The ethylacetate phase was dried over $MgSO_4$ (5.4 gm) followed by solvent removal and titration under isopropyl alcohol:ethyl acetate (2:1 v/v, 6mL) which gave a pale yellow solid (70 mg). The acidic aqueous phase form the partitioning was extracted with dicholormethane (50 mL) with vigorous stirring and then dried over $MgSO_4$ (4.4 gm) and filtered. Solvent removal and titration under isopropyl alcohol:ethylacetate (2:1 v/v, 6 mL) afforded a pale yellow solid (244 mg). HPLC analysis of the yellow solid by reverse-phase HPLC using a C18 5μ column (Phenomenex) and a mobile phase of 60% acetonitrile in water at a flow rate of 1 ml/min gave a peak at 5.1 minutes (90% a.u.c.) and NMR analysis gave the correct spectrum for the isocoumarin (32).

Example 4

Preparation of Further Isocoumarin Derivatives

The isocoumarin derivatives exemplified in TABLE 2 were prepared as according to the instant invention:

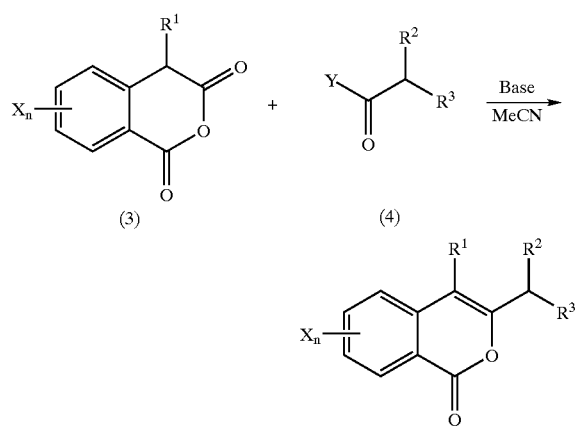

wherein the preparation proceeded by: (A) addition of the anhydride (3) into a solution containing the activated carboxylic acid (4) and base; or (B) addition of anhydride (3) into base via syringe followed by addition of activated carboxylic acid (4). A standard work-up procedure consisted of a 1N HCl wash to remove the base, a saturated $NaHCO_3$ wash to remove any dimerized byproduct, and a saturated NaCl wash to remove water from the organic phase, followed by $NaSO_4$ drying and stripping of the solvent.

TABLE 2

| Product | Compound (3) | Proc. | Base | Time | Temp. | % Yield |
|---|---|---|---|---|---|---|
| ![product structure with MeO, phosphonate OEt groups] | ![compound 33 structure with imidazole and phosphonate] (33) | A | TEA | 5 hr | 50° C. | 73 |

TABLE 2-continued

| Product | Compound (3) | Proc. | Base | Time | Temp. | % Yield |
|---|---|---|---|---|---|---|
| (34) | | A | TEA | 2.3 hr | 50° C. | 76 |
| (35) | | A | TEA | 5 hr | 50° C. | 91 |
| (36) | | A | TEA | 5 hr | 50° C. | Inc.† |
| (37) | | B | TMG | 1 hr | 0° C. | 51 |

†reaction not run to completion within reaction time.

In addition, diketene,

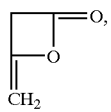

was used instead of a compound of formula (4) to react with 6,8-dimethoxy-isochroman-1,3-dione (25) to produce the isocoumarin of formula (38):

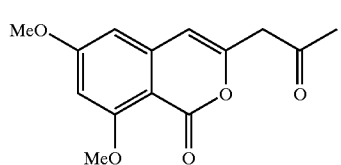
(38)

Self condensation products were also identified in the above reactions. Thus, in addition to previously described self-condensation product, the anhydrides:

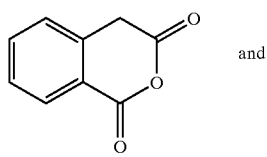
(40)

and

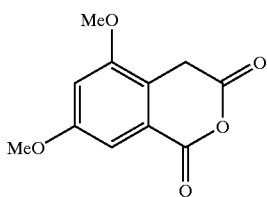
(41)

give rise respectively to the self-condensation products:

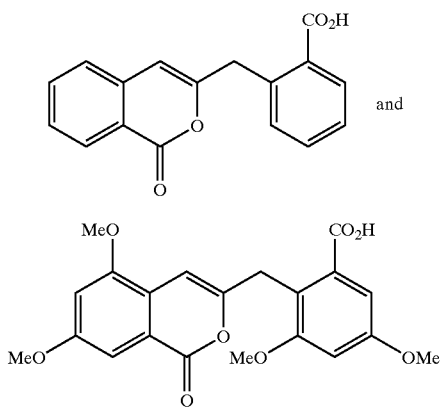

(42)

and (43)

In addition to the forgoing, additional exemplifications of the $R^3$ group of the activated carbonyl compound (4) include, but are not limited to, —$CONH_2$, —$SOCH_3$, —$NO_2$, —NC, and —N═C—$C_6H_6$. Additional exemplifications of the activated carbonyl compound (4) include, but are not limited to:

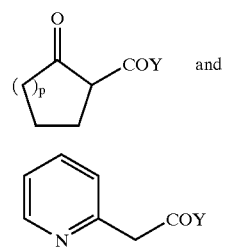

(44)

and (45), wherein the product isocoumarin derivatives are respectively:

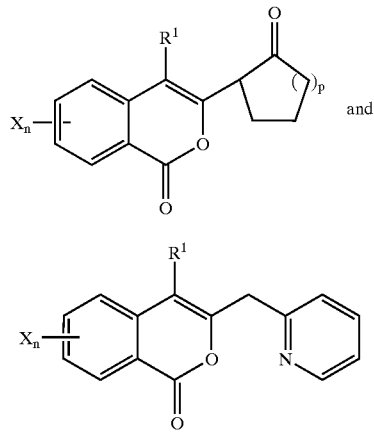

(46)

and (47), and $R^1$, Y and $X_n$ are as previously defined and p is an integer from 1 to 4.

The isocoumarin derivatives produced by the methods of the instant invention may also serve as substrates for the preparation of other isocoumarin analogs. E.g., wherein the activated carbonyl compound is:

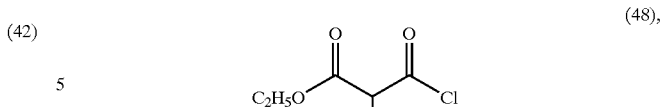

(48), the resulting isocoumarin derivative is:

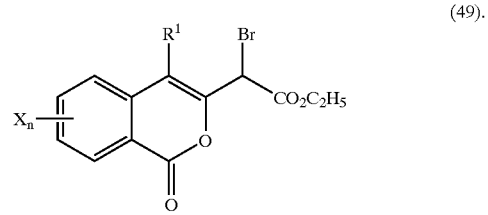

(49).

The compound (49) is used as a substrate in the formation of further isocoumarin analogs:

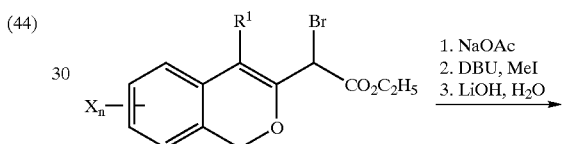

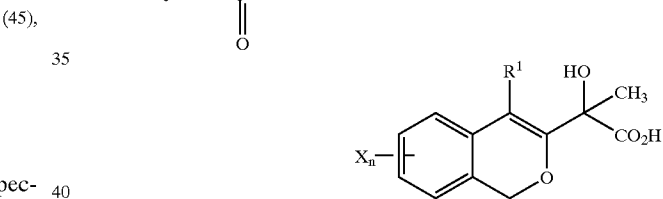

(50)

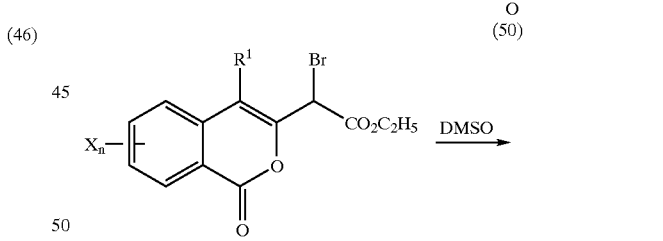

(51)

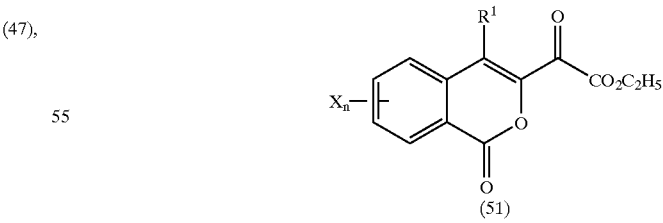

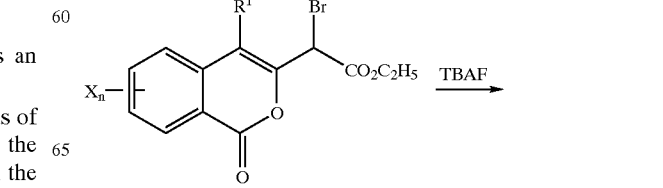

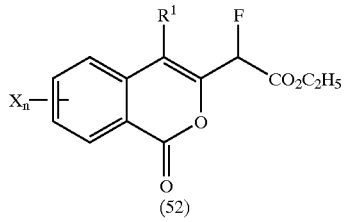

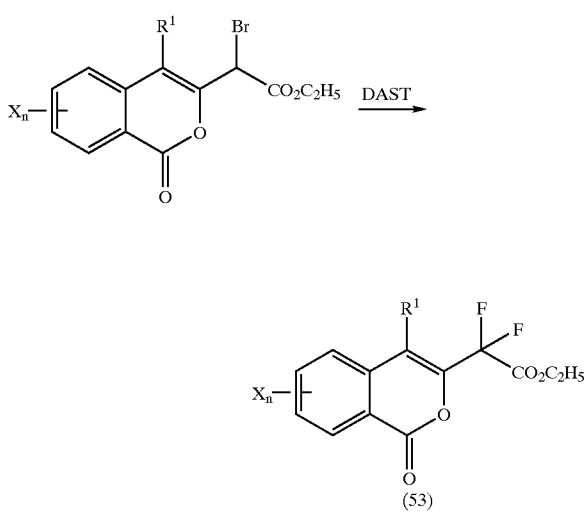

Example 5

Preparation of 2-Carboxymethyl-4,6-dimethoxybenzoic Acid

A. Synthesis of Diethylester Intermediate

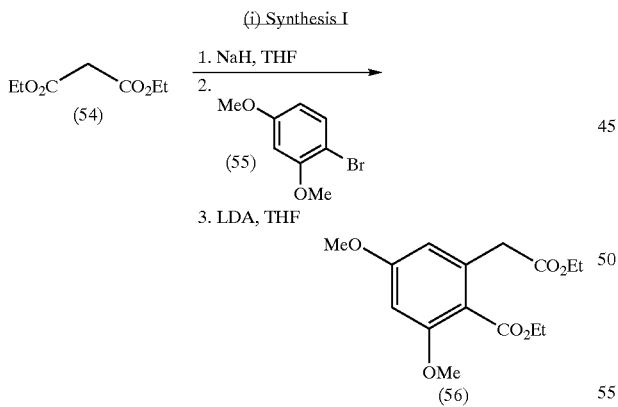

An oven dried 250 mL 3-neck round bottomed flask, equipped with a nitrogen inlet, magnetic stir bar, thermocouple and rubber septa, was charged with NaH (0.8 gm) and 50 mL dry tetrahydrofuran (THF). This suspension was stirred at ambient temperature and diethylmalonate (54) was added over 5 minutes dropwise via syringe. 1-Bromo-2,4-dimethoxybenzene (55) (1.08 g), was added in one portion via syringe to the stirring solution. The flask was then cooled to below −20° C. by an ethanol/$H_2O$/$CO_2$ bath. To a separate oven dried 100 ml 3-necked round bottomed flask, equipped with a rubber septa, magnetic stir bar and nitrogen inlet, was charged a few crystals of 1,10-phenanthroline as indicator and 25 mL dry THF. The flask was cooled to below −60° C. A few drops of n-butyl lithium were added until the brown color of the indicator persisted. The n-butyl lithium (3.05 mL) required for formation of the lithium diisopropylamide (LDA) was then added, followed by slow addition of diisopropylamine (0.91 mL). This solution was stirred for 20 minutes. The LDA was then added dropwise via cannula over 24 minutes maintaining a temperature between −20 and −30° C. Over 2 hours, 2.5 mL (1 eq) of an estimated 2M solution of LDA was added until an in-process control sample indicated greater than 97% conversion. The reaction was quenched at low temperature with 20 mL of 1.0N HCl solution prior to warming to ambient temperature. The solution was acidified with 1.0N HCl and the two phases separated. The organic fraction was washed with 25 mL 1.0N HCl and then saturated NaCl. The solution was filtered through a plug of $MgSO_4$. After removal of solvent in vacuo, 2.65 g of 2-carboxymethyl-4,6-dimethoxybenzoic acid diethyl ester (56) as a yellow/orange oil (purity 93.2% a.u.c) was obtained. Designations assigned to NMR analysis of the compound of formula (56) are as follows:

$^1$HNMR (250 MHz) in $CDCl_3$

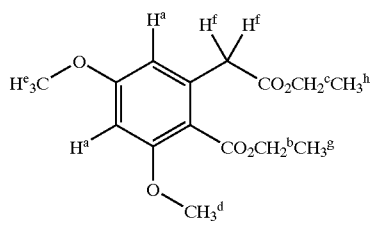

Proton a, 6.40 ppm, (apparent singlet, 2H); proton b, 4.34 ppm (quartet, J=7.2 Hz, 2H); proton c, 4.14 ppm (quartet, J=7.2 Hz, 2H); proton d, 3.817 ppm (singlet, 3H); proton e, 3.811 ppm (singlet, 3H); proton f, 3.66 ppm (singlet, 2H); proton g, 1.35 ppm (triplet, J=7.2 Hz, 3H); proton h, 1.24 ppm (triplet, J=7.2 Hz, 3H).

$^{13}$CNMR (62.5) MHz) in $CDCl_3$

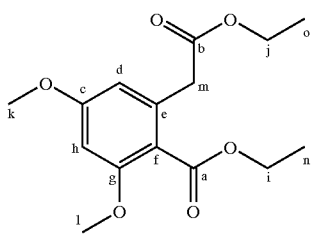

Carbon a, 170.6 ppm; carbon b, 161.4 ppm; carbon c, 167.1 ppm; carbon d, 107.3 ppm; carbon e, 134.8 ppm; carbon f, 116.2 ppm; carbon g, 158.8 ppm; carbon h, 97.7 ppm; carbon I, 60.8 OR 60.77 PPM; carbon j, 60.8 or 60.77 ppm; carbon k, 55.8 ppm; carbon 1, 55.2 ppm; carbon m, 39.5 ppm; carbon n, 14.0 ppm.

(ii) Synthesis II

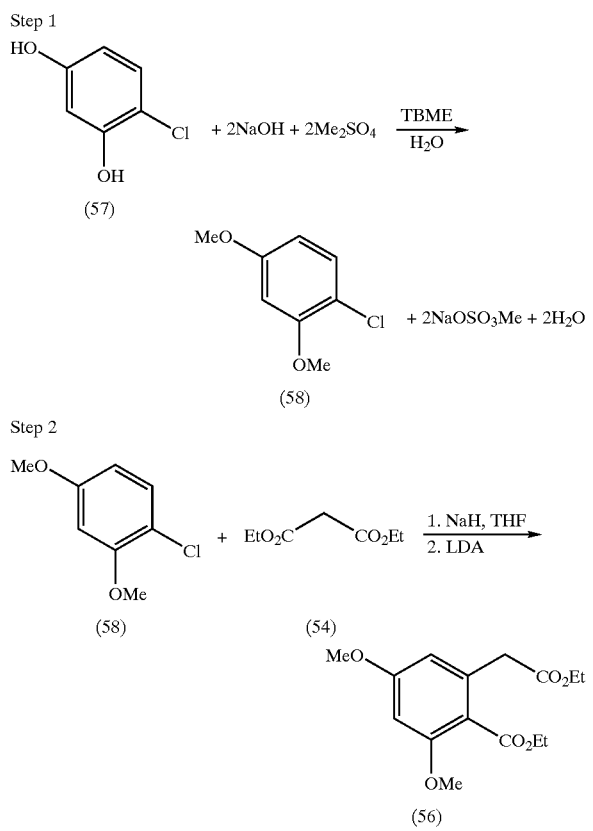

Step 1: Preparation of 1-chloro-2,4-dimethoxybenzene (58):

A 30 L, multi-neck jacketed flask, equipped with a thermocouple, mechanical stirrer, nitrogen purge and peristaltic pump was charged with 4-chlororesorcinol (57) (1.4 kg) and water (4.94 kg). The jacket temperature was set at 20° C. and the reactor was charged with 50% NaOH (1.8 kg) keeping the temperature below 35° C. The reactor was then charged with tert-butyl methyl ether ("TMBE") (5.85 kg) and a nitrogen purge was started through the reactor. The reactor was charged with dimethylsulfate (2.66 kg) and the mixture stirred for approximately 18 hours at ambient temperature. Stirring was stopped and the layers allowed to separate and the aqueous layer was drained from the reactor. Stirring was started and the reactor charged with water (6.68 kg) and 2% ammonium hydroxide (0.76 kg) and the stirring was then stopped and layers allowed to separate. The aqueous layer was drained from the reactor. The TMBE was removed by rotary evaporation, the residue dissolved in heptane (2.7 kg) and the vacuum filtered through silica gel and solvent removed by rotary evaporation. The residue was distilled to remove heptane to give 1-chloro-2,4-dimethoxybenzene (58) as a pale yellow oil.

Step 2: Preparation of 2-carboxymethyl-4,6-dimethoxybenzoic Acid Diethyl Ester (56):

An oven dried 1 L 3-neck round bottom flask, equipped with a nitrogen inlet, magnetic stir bar, and rubber septa, was charged with sodium hydride and THF with stirring. Flask was cooled by EtOH/H$_2$O/CO$_2$ bath to ~0° C. and to this stirring slurry was added via syringe pump diethylmalonate (54) (23.01 gm) over 40 minutes. To this clear stirring solution was added 1-chloro-2,4-dimethoxybenzene (58) (42.6 gm) over 5 minutes. The flask was cooled to below −20° C. by addition of more dry ice to the bath. Lithium diisopropylamide ("LDA") (2M, 100 mL) was added via syringe pump over 67 minutes maintaining an internal temperature of −28 to −20° C. The reaction mixture was stirred for 45 minutes. The dry ice bath was removed and the water (200 mL) was added slowly to the stirring solution. The reaction was then allowed to warm to ambient temperature. The flask contents were transferred to a separatory funnel and the lower aqueous phase was drained. The organic layer was washed with water (2×100 mL). The combined aqueous layers were back extracted with MTBE (100 mL). The combined organic layers were collected and washed with 1 N HCl (2×150 mL), water (100 mL) and brine (100 mL). The organic layer was dried by stirring overnight with MgSO$_4$. The drying agent was filtered off and the solvent was removed in vacuo to give 44.67 g. An oily liquid separated which was presumed to be the mineral oil from the sodium hydride dispersion. The crude product was diluted with MTBE (500 mL) and stirred with 25 g of Darco and 25 g of basic alumina for 2 hours. The mixture was filtered through Celite to give a light yellow colored solution. The filter cake was washed with MTBE and the solvent removed in vacuo to give 37.62 g of 2-carboxymethyl-4,6-dimethoxybenzoic acid diethyl ester (56) as an oil (purity 97.4% a.u.c).

(iii) Synthesis III

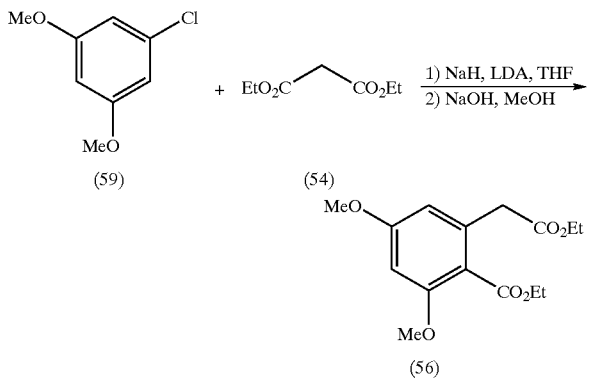

A 100 mL flask, equipped with a magnetic stirbar, thermocouple, and nitrogen inlet, was charged with sodium hydride (1.12 g, 28.00 mmol) and THF (10 mL). The mixture was cooled in an ice/water bath. A solution of (59) (0.82 g, 4.746 mmol) in THF (1.5 mL) was added. The vial and syringe were rinsed with THF (1.0 mL). Diethyl malonate (54) (3.04 g, 18.98 mmol) was added over 6 min, keeping the temperature below 5° C. The vial and syringe were rinsed with THF (1.0 mL). Lithium diisopropylamide (2.8 mL, 5.6 mmol, 2.0 M) was added to the mixture over 1 h, keeping the temp below 5° C. An in-process check by HPLC showed the reaction to be complete. The reaction was quenched with 1.0 N HCl (35 mL). The layers were separated and the aqueous layer was extracted twice with MTBE. The organic extracts were combined and the volatiles were removed by rotary evaporation. The residue was dissolved in methanol (20 mL) and 50% sodium hydroxide in water (2.0 mL, 37.88 mmol) was added. The mixture was stirred overnight at ambient temperature. An in-process check by HPLC showed the reaction to be complete. The mixture was filtered. The flask and solids were washed with methanol (10 mL). The solids were discarded. The filtrate was reduced by rotary evaporation. The residue was dissolved in water (25 mL) and the resulting aqueous solution was washed twice with MTBE. The organic layers were discarded and the aqueous layer was acidified with conc HCl until pH<2. The aqueous layer was extracted twice with ethyl acetate. The organic portions were combined and washed with brine. The volatiles were removed by rotary evaporation to give a tan powder. The $^1$H NMR of this material was identical to an authentic sample of compound (56).

B. Formation and Isolation of 2-Carboxymethyl-4, 6-dimethoxybenzoic Acid (60)

(i) Method I

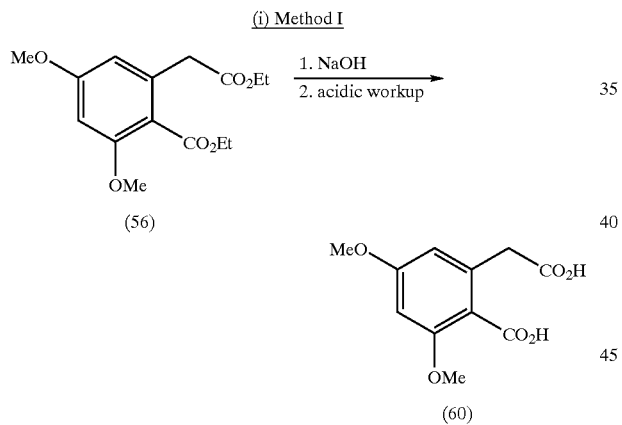

(56)

(60)

A 2-necked 250 mL round bottomed flask equipped with a stir bar and a reflux condenser was charged with the diethyl ester of formula (56) (2.65 gm) and ethanol (100 mL). As the solution was stirred, 10 ml of 10% NaOH was added dropwise. The solution darkened and was stirred at ambient temperature for 105 min. Analysis of an in-process control (IPC) sample revealed 86.7% conversion to the monoester. After heating the solution at reflux 3.5 hrs, only 10.3% conversion into the diacid (60) was observed. Conversion was monitored by reverse phase HPLC with a C18 5μ column and a mobile phase of 60% acetonitrile in water. NaOH as a 10% solution (20 mL) was added. After 1 additional hour of reflux, analysis of an IPC sample revealed 28.6% conversion to the diacid (60). After stirring overnight at ambient temperature, no further reaction was observed. The solution contained fine suspended solids. The solution was heated to reflux and 20% lithium hydroxide solution (12 mL) was added and the solution clarified. After 15 minutes, analysis of an IPC sample revealed 67.2% conversion. Solid NaOH (3 g) was added and stirred for 4.75 hours resulting in a 94.8% conversion to the diacid (60).

The solvent volume was reduced in vacuo resulting in a reddish solution with particulate matter. The aqueous solution was washed twice with 25 mL ethyl acetate to remove non-acidic byproducts. The organic phases were extracted with 25 mL of saturated NaHCO$_3$. The combined alkaline aqueous solutions were placed in a clean 250 mL round bottomed flask and acidified slowly with 12N HCl to an endpoint of pH 1 as determined by pH paper. The solution was extracted with ethyl acetate (2×50 mL, 1×25 mL) and the organic layers were combined and washed with 25 mL saturated NaCl solution, dried by passing through a plug of MgSO$_4$, and stripped of solvent to give 2-carboxymethyl-4,6-dimethoxybenzoic acid (60) as an orange solid (0.90 g, purity 88.3% a.u.c.). Designations assigned to NMR analysis of the compound of formula (60) are as follows:

$^1$HNMR (250 MHz) in 10% CD$_3$OD/CDCl$_3$

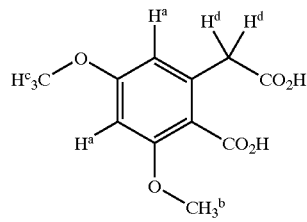

Proton a, 6.63 ppm (apparent singlet, 2H); proton b, 3.83 ppm (singlet, 3H); proton c, 3.77 ppm (singlet, 3H); proton d, 3.73 ppm (singlet, 2H).

$^{13}$CNMR (62.5 MHz) in 10% CD$_3$OD/CDCl$_3$

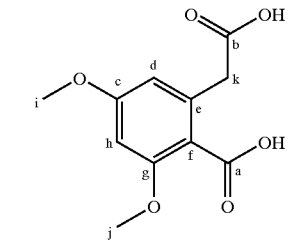

Carbon a, 173.4 ppm; carbon b, 168.8 ppm; carbon c, 162.2 ppm; carbon d, 108.8 ppm; carbon e, 137.7 ppm; carbon f, 113.7 ppm; carbon g, 159.4 ppm; carbon h, 97.7 ppm; carbon I, 56.1 or 55.3 ppm; carbon j, 56.1 or 55.3 ppm; carbon k, 40.6 ppm.

(ii) Method II

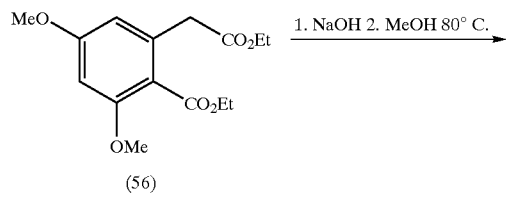

(56)

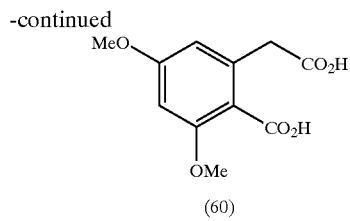

(60)

A 1 L 3-neck RB flask, equipped with a magnetic stir bar, thermocouple, heating mantle, reflux condenser, and rubber septa with 18 ga. needle for pressure release, was charged with (56) and methanol and stirred until homogeneous. While at ambient temperature, 20% sodium hydroxide (231 mL) was added raising internal temperature to approximately 56° C. The heating mantle was set to 80° C. and the solution became yellow and a solid formed at 38 minutes of reflux. The reaction was held at reflux for a total of 2.25 hours when the reaction was cooled to ambient temperature and isopropyl alcohol (100 mL) was added to the slurry and stirred for 15 minutes. The solid product was filtered and the cake washed with isopropyl alcohol until the filtrate ran colorless.

The solid was dissolved in deionized water (250 mL) and filtered to remove insoluble solids. The basic aqueous solution was charged to a flask and acidified with 12N HCl (10 mL). The product crystallized out of solution and was filtered through a fritted glass funnel. The filter cake was rinsed with deionized water and MTBE. The product dried on funnel with nitrogen blanketing for 15 minutes, collected and dried under vacuum at 50° C. overnight. The collected filtrates were stripped of solvent and then acidified with 12N HCl. The product crashed out of solution as flakes. Ethyl acetate was added to dissolve most of the solids, filtered and the phases were separated whereupon the organic phase was washed with brine and dried over $MgSO_4$ for 1 hour. Several grams of Darco were then added and stirred for 15 minutes then filtered. The solvent was removed and then placed on the high vacuum for several minutes. Crude (60) (4.26 g) was collected (54.1% pure). The solid was slurried in a small amount of ethyl acetate and then filtered and dried to give 2.42 g of slightly off-white crystals with a purity of 74.5%.

Example 6

Preparation of 6,8-Dimethoxyisochroman-1,3-dione (25)

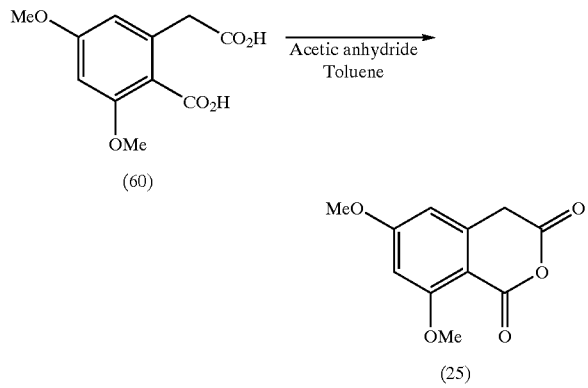

2-Carboxymethyl-4,6-dimethoxybenzoic acid (60) (3.97 gm) was stirred in toluene (40.0 mL) at ambient temperature in a 100 mL flask with magnetic stirring. Acetic anhydride (1.72 mL) was added and the mixture heated to 110° C. Monitoring by HPLC revealed that the reaction was complete within 2.5 hours. Heat was then removed. Crystallization of 6,8-dimethoxyisochroman-1,3-dione (25) occurred as the solution cooled. The mixture was cooled to 2° C. After a short hold time, yellow crystalline solids were filtered, washed with fresh toluene and then dried on high vacuum. 6,8-Dimethoxyisochroman-1,3-dione (25) (3.05 g) was isolated as a yellow crystalline solid.

Example 7

Preparation of 2-Carboxymethyl-3,5-Dimethoxy-Benzoic Acid Diethyl Ester (61)

Figure 3:
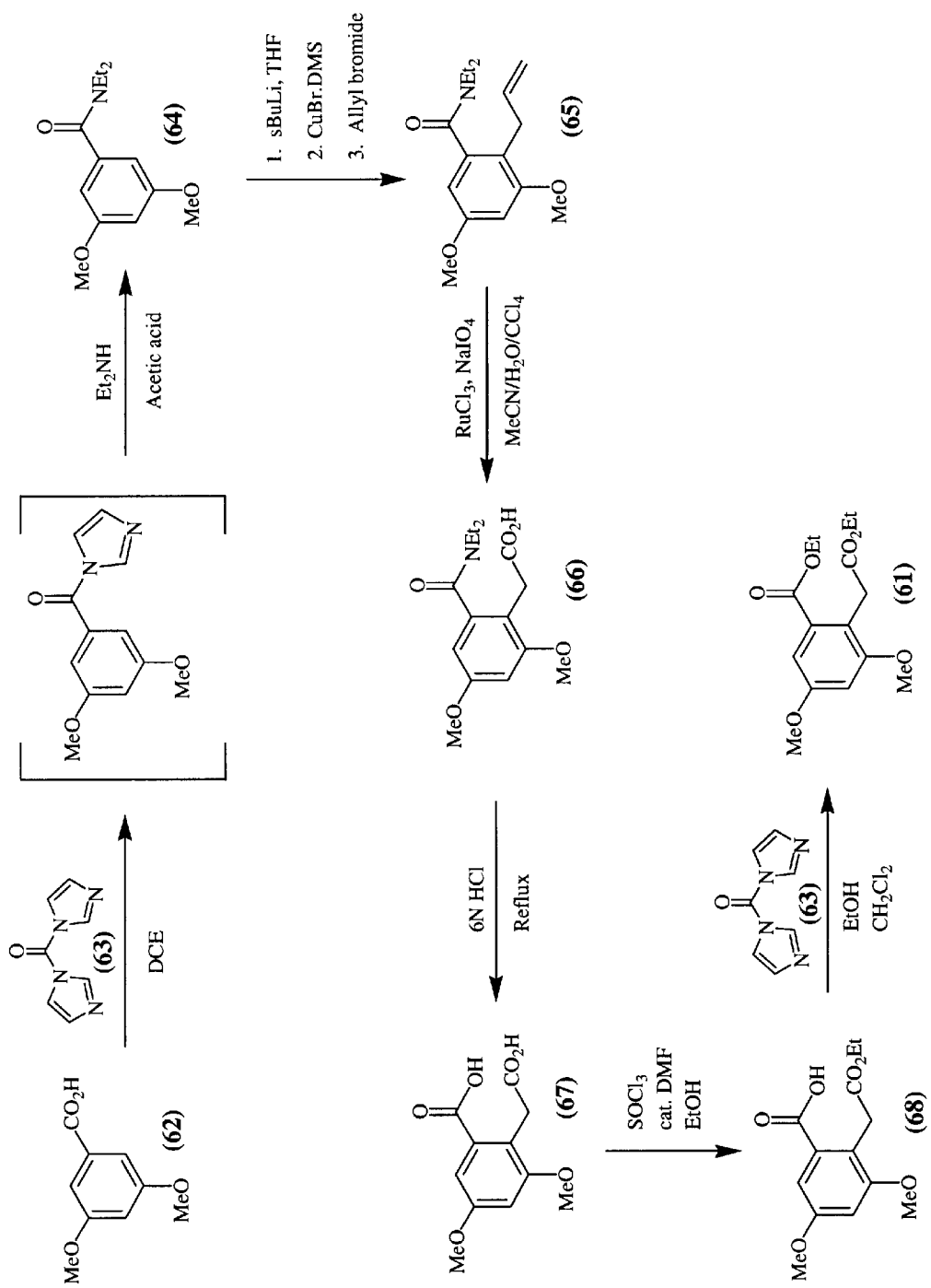
FIG. 3: Summary of the synthesis of 2-carboxy-3,5-dimethoxy benzoic acid.

A summary of the overall synthesis of 2-carboxymethyl-3,5-dimethoxy benzoic acid (61) is shown in FIG. 3. The first step is the synthesis of 3,5-dimethoxy-N,N-diethylbenzamide (64). 3,5-Dimethoxy benzoic acid (62) (10.0 g, Acros Organics) and dichloroethane (105 ml) were added to an oven dried 250 ml 3-neck round-bottom flask, equipped with a nitrogen inlet, magnetic stir bar, thermocouple and rubber septum. The mixture was stirred at ambient temperature and carbonyldiiumidazole (63) (9.79 g) was added in one portion. Diethylamine (6.25 ml) was charged in the reactor followed by acetic acid (3.3 ml). The reaction was set to reflux (75° C.) for 2¼ hours. The reaction cooled and more carbonyldiimidazole (63) (8.9 g) was added and stirred at ambient temperature for 16 hr. An additional amount of diethylamine (5 ml) was added and the reaction was warmed to 50° C. and stirred for 22 hr. Additional carbonyldiimidazole (63) and diethylamine were added over 2 days at 50° C. until there was a 97% conversion to 3,5-dimethoxy-N,N-diethylbenzamide (64). The product was isolated was washing the organic layer with 1N HCl then drying and evaporating the organic layer in vacuo to produce as dark peach liquid that on purification by silica gel chromatography (50:50 ethyl acetate/heptane) yielded 13.83 g of (64) as a pale yellow oil (purity 92.7% a.u.c.).

The second step is the production of 2-allyl-N,N-3,5-dimethoxy-benzamide (65). A catalytic amount of 1,10-phenanthroline as indicator and TBF (20 ml) were charged in a 3-neck 100 ml round-bottom flask equipped with a stir bar. The reactor was cooled to −70° C. under nitrogen purge. Freshly titrated s-BuLi (10.5 ml) was charged dropwise until a purple/brown color persisted, then the full charge of base was added. Amide (64) (2.0 g) was dissolved in THF and slowly added to the s-BuLi solution over 30 min. Copper bromide dimethylsulfide complex (2.53 g) was charged as a single portion and the reaction stirred for 5 min. Allyl bromide (0.88 ml) was charged to the reactor over 10 min and then stirred for an additional 70 min. An in-process control showed an 85.9% conversion to (65). The reaction was poured into 50 ml of 1N HCl and the product was extracted with ethyl acetate twice and the organic layers washed with 50 ml water. An insoluble solid formed and was filtered out. The organic layer was separated and washed with saturated NaCl and then dried over $MgSO_4$. The drying agent was filtered off and solvent removed in vacuo to give the crude product as a brown oil. Purification by silica gel chromatography (20:80 ethyl acetate/heptane) yielded 1.0 g of (65) as an oil (purity 87.9 a.u.c.).

The third step is preparation of (2-diethylcarboxamoyl-4,6-dimethoxy-phenyl)-acetic acid (66). Compound (65) (0.92 g), acetonitrile (19.8 ml), water (12.6 ml) and $CCl_4$ (12.6 ml) were charged to a 3-necked 50 ml round-bottom flask. $RuCl_3$ (0.69 g) and Sodium periodate (4.73 g) was charged in three portions over 3.5 hr and stirred vigorously. The reaction completed in 3 hr wherein the mixture was filtered through Celite and the cake rinsed with ethyl acetate (25 ml). The filtrate was charged to a separatory funnel and the phases were split. The organic layer was washed with water (15 ml). The aqueous layers were combined and extracted with ethyl acetate (15 ml). The combined organic layers were dried over magnesium sulfate and removed in vacuo to yield 0.88 g crude product. Crude (66) was purified by preparative HPLC (50% water/acetonitrile) to afford 241 mg of (66) (97.2% a.u.c.).

The fourth step is preparation of 2-carboxymethyl-3,5-dimethoxy-benzoic acid (67). Compound (66) (0.130 g), water (2 ml) and 12 N HCl (2 ml) were charged to a screw-cap tube. The tube was stirred and heated to reflux for 2.5 hr. Upon cooling a solid formed. The solid was dissolved in ethyl acetate and aqueous layer was extracted twice with ethyl acetate. The combined organic layers were washed with 1N HCl and brine, then dried over magnesium sulfate and solvent removed in vacuo to give 85.5 mg of (67) as a tan solid (94.8 a.u.c.).

In the final step, compound (67) (85.5 mg) and ethanol (5 ml) were charged to an oven dried round bottom flask. A catalytic amount of dimethylformamide (1 drop) was charged followed by thionyl chloride (0.26 ml). The reaction was stirred overnight and the solvent then removed in vacuo. The reaction was taken into dichloromethane (1 ml) and carbonyldilmidazole (63) (65 mg) was charged in a single portion and stirred for 25 min. Anhydrous ethanol (5 ml) was added and stirred overnight. Additional carbonyldiimidazole (63) was charged, followed by more ethanol and the reaction stirred for 2 hr. The solvent was removed from the reaction and the residue was taken into ethyl acetate. The organic phase was washed twice with 1N HCl and brine. The organic layer was dried over magnesium sulfate and solvent removed in vacuo. The crude product was purified by preparative TLC (49.9:49.9:0.2 ethyl acetate/heptane/acetic acid) to give 8.5 ml of (61) as a tan oil (94.8% a.u.c.).

Example 8

Regioselectivity of Homophthalate Ester Formation

The amount of regioisomeric homophthalate ester being produced was verified by analysis of crude benzyne reaction mixtures of a 1-halo-2,4-dimethoxybenzene and dimethylmalonate. HPLC analysis. Samples were analyzed by reverse-phase HPLC using a C18 5μ column and a mobile phase of 1:1acetonitrile and water. Quantification was by calculation of peak area of UV detection at 210 to 300 nm. Using photo diode array for peak identity comparison, no 2-carboxymethyl-3,5-dimethoxy-benzoic acid diethyl ester (61) could be detected. Thus, based on this level of detection, the reaction of the halobenzene (58) with diethylmalonate produces a single product isomer 2-carboxymethyl-4,6-dimethoxy-benzoic acid diethyl ester (56).

The present invention has been shown by both description and examples. The Examples are only examples and cannot be construed to limit the scope of the invention. One of ordinary skill in the art will envision equivalents to the inventive process described by the following claims that are within the scope and spirit of the claimed invention.

What is claimed is:

1. A process for the preparation of isocoumarin derivatives of the formula

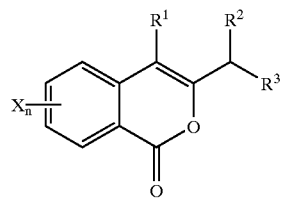

wherein $R^1$ and $R^2$ are independently H, halogen, $C_1$–$C_6$ alkyl, $C_1$–$C_6$ alkenyl, $C_1$–$C_6$ alkynyl, aryl, heteroaryl, $C_1$–$C_6$ acyl, $C_1$–$C_6$ alkoxyl, —$NR^4R^5$, wherein when $R^4$ is H then $R^5$ is sulphonyl or $C_1$–$C_6$ acyl or where $R^4$ and $R^5$ are independently $C_1$–$C_6$ alkyl or $C_1$–$C_6$ acyl; and $R^3$ is an electron withdrawing group;

X is a substituent selected from halo, $C_1$–$C_6$ alkyl, $C_1$–$C_6$ alkenyl, $C_1$–$C_6$ alkynyl, aryl, heteroaryl, $C_1$–$C_6$ acyl, $C_1$–$C_6$ alkoxyl, —$NR^4$ $R^5$, wherein $R^5$ and $R^4$ are as defined above, or $SO_2R^6$, where $R^6$ is $C_1$–$C_6$ alkyl or $C_1$–$C_6$ acyl; and n is an integer from 0 to 4, wherein when n is greater than 1 the X substituents may be the same or different; comprising reacting a homophthalic anhydride of the formula

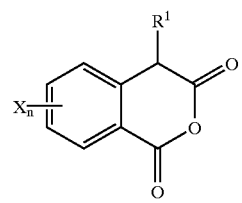

wherein $R^1$, X and n are as defined above; with a carbonyl compound of the formula

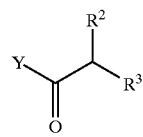

wherein $R^2$ and $R^3$ are as defined above; and Y is an acyl activating substituent; in the presence of a reaction medium comprising a solvent and a base.

2. The process of claim 1, wherein $R^3$ is an electron withdrawing group selected from the group consisting of aryl, hetroaryl, sulfonate, phosphonate, cyano, —$CO_2R^7$, wherein $R^7$ is $C_1$–$C_6$ alkyl, and —$COR^8$, wherein $R^8$ is a halogen.

3. The process of claim 1, wherein $R^3$ is —$CO_2C_2H_5$.

4. The process of claim 1, wherein X is —$OCH_3$.

5. The process of claim 4, wherein n is 2.

6. The process of claim 1, wherein Y is an acyl activating substituent selected from the group consisting of halogen, imidazoyl, pyridyl and aryloxy.

7. The process of claim 6, wherein said halogen is chloro, bromo or iodo.

8. The process of claim 1, wherein Y is imidazoyl.

9. The process of claim 1, wherein said solvent is an aprotic solvent.

10. The process of claim 9, wherein said aprotic solvent is a halogenated or ethereal solvent.

11. The process of claim 9 wherein said aprotic solvent is acetonitrile or N-methyl pyrrolidinone.

12. The process of claim 1, wherein said base is selected from the group consisting of tertiary amine, amidine, amide and tertiary alkoxide bases.

13. The process of claim 1, wherein said base is triethylamine.

14. The process of claim 1, wherein said base is 1,8-diazabicylco[5.4.0]-undec-7-ene.

15. A process for the preparation of isocoumarin derivatives of the formula:

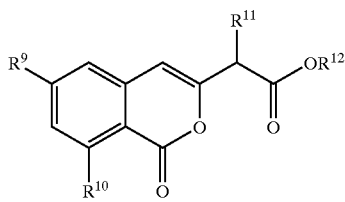

wherein $R^{11}$ and $R^{12}$ are independently $C_1$–$C_6$ alkyl; and $R^9$ and $R^{10}$ are independently $C_1$–$C_6$ alkyl or $C_1$–$C_6$ alkoxy; comprising reacting a homophthalic anhydride of the formula:

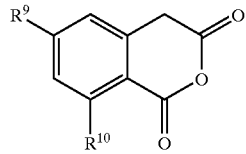

wherein $R^9$ and $R^{10}$ are as defined above; with a carbonyl compound of the formula:

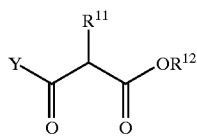

wherein $R^{11}$ and $R^{12}$ are as defined above; and Y is an acyl activating group; in the presence of a reaction medium comprising a solvent and a base.

16. The process of claim 15, wherein Y is an acyl activating group selected from the group consisting of halogen, imidazoyl, pyridyl and aryloxy.

17. The process of claim 16, wherein said halogen is chloro, bromo or iodo.

18. The process of claim 15, wherein Y is imidazoyl.

19. The process of claim 15, wherein said solvent is an aprotic solvent.

20. The process of claim 19, wherein said aprotic solvent is a halogenated or ethereal solvent.

21. The process of claim 19, wherein said aprotic solvent is acetonitrile or N-methyl pyrrolidinone.

22. The process of claim 15, wherein said base is selected from the group consisting of tertiary amine, amidine, amide and tertiary alkoxide bases.

23. The process of claim 15, wherein said base if triethylamine.

24. The process of claim 15, wherein said base is 1,8-diazabicylco[5.4.0]-undec-7-ene.

25. The process of claim 15, wherein $R^{11}$ is methyl, $R^{12}$ is ethyl, and $R^9$ and $R^{10}$ are methoxy and said isocoumarin derivative is:

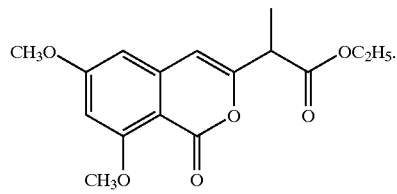

26. The process of claim 25, further comprising removal of the ethyl ester group and a methyl group from said isocoumarin derivative:

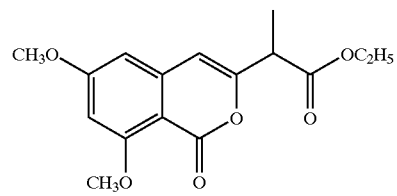

to provide the isocoumarin derivative of the formula:

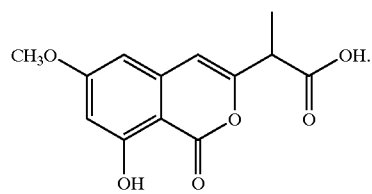

* * * * *